US006733963B2

(12) United States Patent
Hamer et al.

(10) Patent No.: US 6,733,963 B2
(45) Date of Patent: May 11, 2004

(54) METHODS FOR THE IDENTIFICATION OF INHIBITORS OF 3-ISOPROPYLMALATE DEHYDRATASE AS ANTIBIOTICS

(75) Inventors: Lisbeth Hamer, Durham, NC (US); Kiichi Adachi, Durham, NC (US); Todd DeZwaan, Apex, NC (US); Sze-Chung Lo, Durham, NC (US); Maria Victoria Montenegro-Chamorro, Colombia, NC (US); Sheryl Frank, Durham, NC (US); Blaise Darveaux, Hillsborough, NC (US); Sanjoy Mahanty, Chapel Hill, NC (US); Ryan Heiniger, Raleigh, NC (US); Amy Skalchunes, Raleigh, NC (US); Huaqin Pan, Apex, NC (US); Rex Tarpey, Apex, NC (US); Jeffrey Shuster, Chapel Hill, NC (US); Matthew M. Tanzer, Durham, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 10/010,227

(22) Filed: Dec. 6, 2001

(65) Prior Publication Data

US 2003/0143657 A1 Jul. 31, 2003

(51) Int. Cl.[7] .......................... C12Q 1/00; C12P 21/06; C12N 1/20; A31K 31/18; C07H 21/04

(52) U.S. Cl. ....................... 435/4; 435/69.1; 435/252.2; 514/601; 514/603; 514/924; 536/23.1; 536/23.7

(58) Field of Search ....................... 435/4, 69.1, 252.2, 435/320.1; 514/256, 601, 603, 924; 536/23.1, 23.7

(56) References Cited

U.S. PATENT DOCUMENTS

| | | | |
|---|---|---|---|
| 4,920,109 A | 4/1990 | Onishi et al. | |
| 4,920,111 A | 4/1990 | Onishi et al. | |
| 4,920,112 A | 4/1990 | Onishi et al. | |
| 4,920,113 A | 4/1990 | Onishi et al. | |
| 4,921,844 A | 5/1990 | Onishi et al. | |
| 5,976,848 A | 11/1999 | Davis et al. | |
| 5,998,420 A | * 12/1999 | Grandoni | 514/256 |
| 6,074,830 A | 6/2000 | Bacot et al. | |

OTHER PUBLICATIONS

IUBMB Enzyme Nomenclature, Chem. qmul.ac.uk.iubmb/Enzyme/E.C. 4.2.1.33html. Created 1972,modified 1976, p. 1 of 1.*

Bode et al., J. Basic Microbiology, 1991, 31(1), pp. 21–26.*

Hawkes et al. Z. Naturforsch, 1993, vol. 48c, pp. 364–368.*

Rubin et al. Gene, 1994, 140, pp. 131–135.*

Aufauvre–Brown, Agnes et al., "*Aspergillus fumigatus chsE*: A Gene Related to CHS3 of *Saccharomyces cerevisiae* and Important for Hyphal Growth and Conidiophore Development but Not Pathogenicity." Fungal Genetics and Biology (1997) 21: 141–152.

Tang, Christoph M. et al., "Virulence Studies of *Aspergillus nidulans* Mutants Requiring Lysine or p–Aminobenzoic Acid in Invasive Pulmonary Aspergillosis." Infection and Immunity (194) Dec.: 5255–5260.

Brown, Jeremy S. et al., "Signature–tagged and directed mutagenesis identify PABA synthetase as essential for *Aspergillus fumigatus* pathocenicity." Molecular Microbiology (2000) 36(6): 1371–1380.

D'Enfert, Christophe., "Attenuated Virulence of Uridine–Uracil Auxtrophs of *Aspergillus fumigatus*." Infection and Immunity (1996) Oct.: 4401–4405.

Hensel, M. et al,"The role of the *Aspergillus fumigatus* areA gene in invasive pulmonary aspergillosis." Mol Gen enet (1998): 553–557.

Shibuya, Kazutoshi et al., "Histopathology of experimental invasive pulmonary aspergillosis in rats: Pathological comparison of pulmonary lesions induced by specific virulent factor deficient mutants." Microbial Pathogenesis (1999) 27: 123–131.

Smith, Joanne M. et al., "Virulence of *Aspergillus fumigatus* Double Mutants Lacking Restrictocin and an Alkaline Protease in a Low–Dose Model of Invasive Pulmonary Apergillosis." Infection and Immunity (1994) Dec.: 5247–5254.

Reichard, U. et al, Virulence of an aspergillopepsin–deficient mutant of *Aspergillus fumigatus* and evidence for another aspartic proteinase linked to the fungal cell wall. J Med Vet Mycol (1997) May–Jun.; 35 (3): 189–96.

Satyanarayana, T. et al., "Biosynthesis of Branched–Chain Amino Acids in Yeast: Regulation of Leucine Biosynthesis in Prototrophic and Leucine Auxotrphic Strains." Journal of Bacteriology (1968) Dec.: 2018–2024.

Satyanarayana, T. et al., "Biosynthesis of Branched–Chain Amino Acids in Yeast: Correlation of Biochemical Blocks and Genetic Lesions in Leucine Auxotrophs." Journal of Bacteriology (1968) Dec.: 2012–2017.

(List continued on next page.)

*Primary Examiner*—Jon P. Weber
*Assistant Examiner*—Kailash C. Srivastava
(74) *Attorney, Agent, or Firm*—Deborah H. Spencer; Timothy G. Hofmeyer; Laura L. Kiefer

(57) ABSTRACT

The present inventors have discovered that 3-Isopropylmalate dehydratase is essential for fungal pathogenicity. Specifically, the inhibition of 3-Isopropylmalate dehydratase gene expression in fungi results in no signs of successful infection or lesions. Thus, 3-Isopropylmalate dehydratase can be used as a target for the identification of antibiotics, preferably antifungals. Accordingly, the present invention provides methods for the identification of compounds that inhibit 3-Isopropylmalate dehydratase expression or activity. The methods of the invention are useful for the identification of antibiotics, preferably antifungals.

4 Claims, 3 Drawing Sheets

OTHER PUBLICATIONS

Kohlhaw, Gunter B. et al. " Isopropylmalate Dehydratase from Yeast." Methods in Enzymology 166: 423–429.

Brisco, Paula R. G. et al., "Cloning Disruption and Chromosomal Mapping of Yeast LEU3, a Putative Regulatory Gene." Genetics (1987) Jan. 115: 91–99.

Calvo, J. M. et al. "Isolation and Chemical Estimation of α–Isopropylmalate and β–Isopropylmalate." Methods in Enzymology (1970) 107: 791–793.

Bigelis, Ramunas et al. "Yeast α–Isopropylmalate Isomerase." The Journal of Biological Chemistry (1976) Jun., 251: 3545–3552.

Bigelis, Ramunas et al., "Purification of Yeast α–Isopropylmalate Isomerase." The Journal of Biological Chemistry (1975) Jun., 250: 4315–4321.

Baichwal, Vijay et al., "Leucine Biosynthesis in Yeast." Current Genetics (1983) 7: 369–377.

Friden, Phillip et al., "LEU3 of *Saccharomyces cerevisiae* Encodes a Factor for Control of RNA Levels of a group of Leucine–Specific Genes." Molecular and Cellular Biology (1987) Aug.: 2708–2717.

Evers et al.; "Strategies Towards a Better Understanding of Antibiotics Action:Folate Patheway Inhibition in *Haemophilus influenzae* as an Example"; Electrophoresis; 1998; vol. 19; pp. 1980–1988.

Skala et al.; Complete Sequence of the *Saccharomyces cerevisiae* LEU1 Gene Encoding Isopropylmalate isomerase; YEAST; 1991; vol. 7; pp. 281–285.

* cited by examiner

Minimal Media

Minimal Media + L-leucine

METHODS FOR THE IDENTIFICATION OF INHIBITORS OF 3-ISOPROPYLMALATE DEHYDRATASE AS ANTIBIOTICS

FIELD OF THE INVENTION

The invention relates generally to methods for the identification of antibiotics, preferably antifungals that affect the biosynthesis of L-leucine.

BACKGROUND OF THE INVENTION

Filamentous fungi are the causal agents responsible for many serious pathogenic infections of plants and animals. Since fungi are eukaryotes, and thus more similar to their host organisms than, for example bacteria, the treatment of infections by fungi poses special risks and challenges not encountered with other types of infections. One such fungus is *Magnaporthe grisea*, the fungus that causes rice blast disease. It is an organism that poses a significant threat to food supplies worldwide. Other examples of plant pathogens of economic importance include the pathogens in the genera Agaricus, Alternaria, Anisogramma, Anthracoidea, Antrodia, Apiognomonia, Apiosporina, Armillaria, Ascochyta, Aspergillus, Bipolaris, Bjerkandera, Botryosphaeria, Botrytis, Ceratobasidium, Ceratocystis, Cercospora, Cercosporidium, Cerotelium, Cerrena, Chondrostereum, Chryphonectria, Chrysomyxa, Cladosporium, Claviceps, Cochliobolus, Coleosporium, Colletotrichium, Colletotrichum, Corticium, Corynespora, Cronartium, Cryphonectria, Cryptosphaeria, Cyathus, Cymadothea, Cytospora, Daedaleopsis, Diaporthe, Didymella, Diplocarpon, Diplodia, Discohainesia, Discula, Dothistroma, Drechslera, Echinodontium, Elsinoe, Endocronartium, Endothia, Entyloma, Epichloe, Erysiphe, Exobasidium, Exserohilum, Fomes, Fomitopsis, Fusarium, Gaeumannomyces, Ganoderma, Gibberella, Gloeocercospora, Gloeophyllum, Gloeoporus, Glomerella, Gnomoniella, Guignardia, Gymnosporangium, Helminthosporium, Herpotrichia, Heterobasidion, Hirschioporus, Hypodermella, Inonotus, Irpex, Kabatiella, Kabatina, Laetiporus, Laetisaria, Lasiodiplodia, Laxitextum, Leptographium, Leptosphaeria, Leptosphaerulina, Leucytospora, Linospora, Lophodermella, Lophodermium, Macrophomina, Magnaporthe, Marssonina, Melampsora, Melampsorella, Meria, Microdochium, Microsphaera, Monilinia, Monochaetia, Morchella, Mycosphaerella, Myrothecium, Nectria, Nigrospora, Ophiosphaerella, Ophiostoma, Penicillium, Perenniporia, Peridermium, Pestalotia, Phaeocryptopus, Phaeolus, Phakopsora, Phellinus, Phialophora, Phoma, Phomopsis, Phragmidium, Phyllachora, Phyllactinia, Phyllosticta, Phymatotrichopsis, Pleospora, Podosphaera, Pseudopeziza, Pseudoseptoria, Puccinia, Pucciniastrum, Pyricularia, Rhabdocline, Rhizoctonia, Rhizopus, Rhizosphaera, Rhynchosporium, Rhytisma, Schizophyllum, Schizopora, Scirrhia, Sclerotinia, Sclerotium, Scytinostroma, Septoria, Setosphaera, Sirococcus, Spaerotheca, Sphaeropsis, Sphaerotheca, Sporisorium, Stagonospora, Stemphylium, Stenocarpella, Stereum, Taphrina, Thielaviopsis, Tilletia, Trametes, Tranzschelia, Trichoderma, Tubakia, Typhula, Uncinula, Urocystis, Uromyces, Ustilago, Valsa, Venturia, Verticillium, Xylaria, and others. Related organisms in the classification, oomycetes, that include the genera Albugo, Aphanomyces, Bremia, Peronospora, Phytophthora, Plasmodiophora, Plasmopara, Pseudoperonospora, Pythium, Sclerophthora, and others are also significant plant pathogens and are sometimes classified along with the true fungi. Human diseases that are caused by filamentous fungi include life-threatening lung and disseminated diseases, often a result of infections by *Aspergillus fumigatus*. Other fungal diseases in animals are caused by fungi in the genera, Fusarium, Blastomyces, Microsporum, Trichophyton, Epidermophyton, Candida, Histoplamsa, Pneumocystis, Cryptococcus, other Aspergilli, and others. The control of fungal diseases in plants and animals is usually mediated by chemicals that inhibit the growth, proliferation, and/or pathogenicity of the fungal organisms. To date, there are less than twenty known modes-of-action for plant protection fungicides and human antifungal compounds.

A pathogenic organism has been defined as an organism that causes, or is capable of causing disease. Pathogenic organisms propagate on or in tissues and may obtain nutrients and other essential materials from their hosts. A substantial amount of work concerning filamentous fungal pathogens has been performed with the human pathogen, *Aspergillus fumigatus*. Shibuya et al. (Shibuya, K., M. Takaoka, et al (1999) Microb Pathog 27: 123–31 (PMID: 10455003)) have shown that the deletion of either of two suspected pathogenicity related genes encoding an alkaline protease or a hydrophobin (rodlet) respectively, did not reduce mortality of mice infected with these mutant strains. Smith et al. (Smith, J. M., C. M. Tang, et al. (1994) Infect Immun 62: 5247–54 (PMID: 7960101)) showed similar results with alkaline protease and the ribotoxin restrictocin; *Aspergillus fumigatus* strains mutated for either of these genes were fully pathogenic to mice. Reichard et al. (Reichard, U., M. Monod, et al. (1997) J Med Vet Mycol 35: 189 –96 (PMID: 9229335)) showed that deletion of the suspected pathogenicity gene encoding, aspergillopepsin (PEP) in *Aspergillus fumigatus*, had no effect on mortality in a guinea pig model system, and Aufauvre-Brown et al (Aufauvre-Brown, A., E. Mellado, et al. (1997) Fungal Genet Biol 21: 141–52 (PMID: 9073488)) showed no effects of a chitin synthase mutation on pathogenicity. However, not all experiments produced negative results. Ergosterol is an important membrane component found in fungal organisms. Pathogenic fungi that lack key enzymes in this biochemical pathway might be expected to be non-pathogenic since neither the plant nor animal hosts contain this particular sterol. Many antifungal compounds that affect this biochemical pathway have been described (Onishi, J. C. and A. A. Patchett (1990a, b, c, d, and e) U.S. Pat. Nos. 4,920,109; 4,920,111; 4,920,112; 4,920,113; and 4,921,844, Merck & Co. Inc. (Rahway N.J.)) and (Hewitt, H. G. (1998) *Fungicides in Crop Protection* Cambridge, University Press). D'Enfert et al (D'Enfert, C., M. Diaquin, et al. (1996) Infect Immun 64: 4401–5 (PMID: 8926121)) showed that an *Aspergillus fumigatus* strain mutated in an orotidine 5'-phosphate decarboxylase gene was entirely non-pathogenic in mice, and Brown et al. (Brown, J. S., A. Aufauvre-Brown, et al. (2000) Mol Microbiol 36: 1371–80 (PMID: 10931287)) observed a non-pathogenic result when genes involved in the synthesis of para-aminobenzoic acid were mutated. Some specific target genes have been described as having utility for the screening of inhibitors of plant pathogenic fungi. Bacot et al. (Bacot, K. O., D. B. Jordan, et al. (2000) U.S. Pat. No. 6,074,830, E. I. du Pont de Nemours & Company (Wilmington Del.)) describe the use of 3,4-dihydroxy-2-butanone 4-phosphate synthase, and Davis et al. (Davis, G. E., G. D. Gustafson, et al. (1999) U.S. Pat. No. 5,976,848, Dow AgroSciences LLC (Indianapolis Ind.)) describe the use of dihydroorotate dehydrogenase for potential screening purposes.

There are also a number of papers that report less clear results, showing neither full pathogenicity nor non-pathogenicity of mutants. Hensel et al (Hensel, M., H. N. Arst, Jr., et al. (1998) Mol Gen Genet 258: 553–7 (PMID: 9669338)) showed only moderate effects of the deletion of the area transcriptional activator on the pathogenicity of *Aspergillus fumigatus*.

Therefore, it is not currently possible to determine which specific growth materials may be readily obtained by a pathogen from its host, and which materials may not. We have found that *Magnaporthe grisea* that cannot synthesize their own L-leucine are non-pathogenic on their host organism. To date there do not appear to be any publications demonstrating an anti-pathogenic effect of the knock-out, over-expression, antisense expression, or inhibition of the genes or gene products involved in L-leucine biosynthesis in filamentous fungi. Thus, it has not been shown that the de novo biosynthesis of L-leucine is essential for fungal pathogenicity. And, thus, it would be desirable to determine the utility of the enzymes involved in L-leucine biosynthesis for evaluating antibiotic compounds, especially fungicides. If a fungal biochemical pathway or specific gene product in that pathway is shown to be required for fungal pathogenicity, various formats of in vitro and in vivo screening assays may be put in place to discover classes of chemical compounds that react with the validated target gene, gene product, or biochemical pathway, and are thus candidates for antifungal, biocide, and biostatic materials.

SUMMARY OF THE INVENTION

Surprisingly, the present inventors have discovered that in vivo disruption of the gene encoding 3-Isopropylmalate dehydratase in *Magnaporthe grisea* prevents or inhibits the pathogenicity of the fungus. Thus, the present inventors have discovered that 3-Isopropylmalate dehydratase is essential for normal rice blast pathogenicity, and can be used as a target for the identification of antibiotics, preferably fungicides. Accordingly, the present invention provides methods for the identification of compounds that inhibit 3-Isopropylmalate dehydratase expression or activity. The methods of the invention are useful for the identification of antibiotics, preferably fungicides.

DETAILED DESCRIPTION OF THE INVENTION

Figure 1:
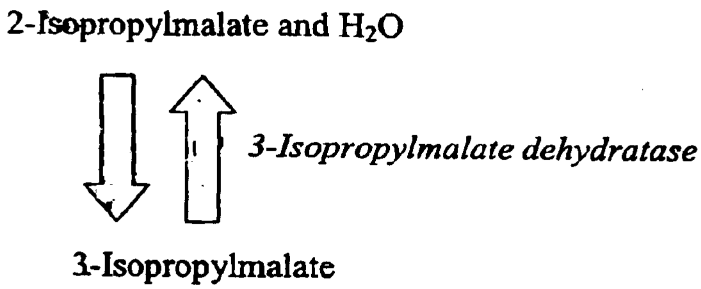
FIG. 1 shows the reaction performed by 3-Isopropylmalate dehydratase (IPMD1) reaction. The Substrates/Products are 2-Isopropylmalate and $H_2O$ and the Product/Substrate is 3-Isopropylmalate. The function of the 3-Isopropylmalate dehydratase enzyme is the interconversion of 2-Isopropylmalate and $H_2O$ to 3-Isopropylmalate. This reaction is part of the L-leucine biosynthesis pathway.

Unless otherwise indicated, the following terms are intended to have the following meanings in interpreting the present invention.

The term "active against" in the context of compounds, agents, or compositions having antibiotic activity indicates that the compound exerts an effect on a particular target or targets which is deleterious to the in vitro and/or in vivo growth of an organism having that target or targets. In particular, a compound active against a gene exerts an action on a target which affects an expression product of that gene. This does not necessarily mean that the compound acts directly on the expression product of the gene, but instead indicates that the compound affects the expression product in a deleterious manner. Thus, the direct target of the compound may be, for example, at an upstream component which reduces transcription from the gene, resulting in a lower level of expression. Likewise, the compound may affect the level of translation of a polypeptide expression product, or may act on a downstream component of a biochemical pathway in which the expression product of the gene has a major biological role. Consequently, such a compound can be said to be active against the gene, against the gene product, or against the related component either upstream or downstream of that gene or expression product. While the term "active against" encompasses a broad range of potential activities, it also implies some degree of specificity of target. Therefore, for example, a general protease is not "active against" a particular gene which produces a polypeptide product. In contrast, a compound which inhibits a particular enzyme is active against that enzyme and against the gene which codes for that enzyme.

As used herein, the term "allele" refers to any of the alternative forms of a gene that may occur at a given locus.

The term "antibiotic" refers to any substance or compound that when contacted with a living cell, organism, virus, or other entity capable of replication, results in a reduction of growth, viability, or pathogenicity of that entity.

The term "binding" refers to a non-covalent or a covalent interaction, preferably non-covalent, that holds two molecules together. For example, two such molecules could be an enzyme and an inhibitor of that enzyme. Non-covalent interactions include hydrogen bonding, ionic interactions among charged groups, van der Waals interactions and hydrophobic interactions among nonpolar groups. One or more of these interactions can mediate the binding of two molecules to each other.

The term "biochemical pathway" or "pathway" refers to a connected series of biochemical reactions normally occurring in a cell, or more broadly a cellular event such as cellular division or DNA replication. Typically, the steps in such a biochemical pathway act in a coordinated fashion to produce a specific product or products or to produce some other particular biochemical action. Such a biochemical pathway requires the expression product of a gene if the absence of that expression product either directly or indirectly prevents the completion of one or more steps in that pathway, thereby preventing or significantly reducing the production of one or more normal products or effects of that pathway. Thus, an agent specifically inhibits such a biochemical pathway requiring the expression product of a particular gene if the presence of the agent stops or substantially reduces the completion of the series of steps in that pathway. Such an agent, may, but does not necessarily, act directly on the expression product of that particular gene.

As used herein, the term "cDNA" means complementary deoxyribonucleic acid.

As used herein, the term "CoA" means coenzyme A.

As used herein, the term "conditional lethal" refers to a mutation permitting growth and/or survival only under special growth or environmental conditions.

As used herein, the term "cosmid" refers to a hybrid vector, used in gene cloning, that includes a cos site (from the lambda bacteriophage). It also contains drug resistance marker genes and other plasmid genes. Cosmids are especially suitable for cloning large genes or multigene fragments.

As used herein, the term "dominant allele" refers to a dominant mutant allele in which a discernable mutant phenotype can be detected when this mutation is present in an organism that also contains a wild type (non-mutant), recessive allele, or other dominant allele.

As used herein, the term "DNA" means deoxyribonucleic acid.

As used herein, the term "ELISA" means enzyme-linked immunosorbent assay.

"Fungi" (singular: fungus) refers to whole fungi, fungal organs and tissues (e.g., asci, hyphae, pseudohyphae, rhizoid, sclerotia, sterigmata, spores, sporodochia, sporangia, synnemata, conidia, ascostroma, cleistothecia, mycelia, perithecia, basidia and the like), spores, fungal cells and the progeny thereof. Fungi are a group of organisms (about 50,000 known species), including, but not limited to, mushrooms, mildews, moulds, yeasts, etc., comprising the kingdom Fungi. They can either exist as single cells or make up a multicellular body called a mycelium, which consists of filaments known as hyphae. Most fungal cells are multinucleate and have cell walls, composed chiefly of chitin. Fungi exist primarily in damp situations on land and, because of the absence of chlorophyll and thus the inability to manufacture their own food by photosynthesis, are either parasites on other organisms or saprotrophs feeding on dead organic matter. The principal criteria used in classification are the nature of the spores produced and the presence or absence of cross walls within the hyphae. Fungi are distributed worldwide in terrestrial, freshwater, and marine habitats. Some live in the soil. Many pathogenic fungi cause disease in animals and man or in plants, while some saprotrophs are destructive to timber, textiles, and other materials. Some fungi form associations with other organisms, most notably with algae to form lichens.

As used herein, the term "fungicide", "antifungal", or "antimycotic" refers to an antibiotic substance or compound that kills or suppresses the growth, viability, or pathogenicity of at least one fungus, fungal cell, fungal tissue or spore.

In the context of this disclosure, "gene" should be understood to refer to a unit of heredity. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. ("Sequence" is used in the similar way in referring to RNA chains, linear chains made of ribonucleotides.) The gene may include regulatory and control sequences, sequences which can be transcribed into an RNA molecule, and may contain sequences with unknown function. The majority of the RNA transcription products are messenger RNAs (mRNAs), which include sequences which are translated into polypeptides and may include sequences which are not translated. It should be recognized that small differences in nucleotide sequence for the same gene can exist between different fungal strains, or even within a particular fungal strain, without altering the identity of the gene.

As used in this disclosure, the terms "growth" or "cell growth" of an organism refers to an increase in mass, density, or number of cells of said organism. Some common methods for the measurement of growth include the determination of the optical density of a cell suspension, the counting of the number of cells in a fixed volume, the counting of the number of cells by measurement of cell division, the measurement of cellular mass or cellular volume, and the like.

As used in this disclosure, the term "growth conditional phenotype" indicates that a fungal strain having such a phenotype exhibits a significantly greater difference in growth rates in response to a change in one or more of the culture parameters than an otherwise similar strain not having a growth conditional phenotype. Typically, a growth conditional phenotype is described with respect to a single growth culture parameter, such as temperature. Thus, a temperature (or heat-sensitive) mutant (i.e., a fungal strain having a heat-sensitive phenotype) exhibits significantly different growth, and preferably no growth, under non-permissive temperature conditions as compared to growth under permissive conditions. In addition, such mutants preferably also show intermediate growth rates at intermediate, or semi-permissive, temperatures. Similar responses also result from the appropriate growth changes for other types of growth conditional phenotypes.

As used herein, the term "$H_2O$" means water.

As used herein, the term "heterologous IPMD1 gene" means a gene, not derived from *Magnaporthe grisea*, and having: at least 50% sequence identity, preferably 60%, 70%, 80%, 90%, 95%, 99% sequence identity and each integer unit of sequence identity from 50–100% in ascending order to SEQ ID NO: 1 or SEQ ID NO: 2; or at least 10% of the activity of a *Magnaporthe grisea* 3-Isopropylmalate dehydratase, preferably 25%, 50%, 75%, 90%, 95%, 99% and each integer unit of activity from 10–100% in ascending order.

As used herein, the term "His-Tag" refers to an encoded polypeptide consisting of multiple consecutive histidine amino acids.

As used herein, the term "HPLC" means high pressure liquid chromatography.

As used herein, the terms "hph", "hygromycin B phosphotransferase", and "hygromycin resistance gene" refer to the *E. coli* hygromycin phosphotransferase gene or gene product.

As used herein, the term "hygromycin B" refers to an aminoglycosidic antibiotic, used for selection and maintenance of eukaryotic cells containing the *E. coli* hygromycin resistance gene.

"Hypersensitive" refers to a phenotype in which cells are more sensitive to antibiotic compounds than are wild-type cells of similar or identical genetic background.

"Hyposensitive" refers to a phenotype in which cells are less sensitive to antibiotic compounds than are wild-type cells of similar or identical genetic background.

As used herein, the term "imperfect state" refers to a classification of a fungal organism having no demonstrable sexual life stage.

The term "inhibitor", as used herein, refers to a chemical substance that inactivates the enzymatic activity of 3-Isopropylmalate dehydratase or substantially reduces the level of enzymatic activity, wherein "substantially" means a reduction at least as great as the standard deviation for a measurement, preferably a reduction by 50%, more preferably a reduction of at least one magnitude, i.e. to 10%. The inhibitor may function by interacting directly with the enzyme, a cofactor of the enzyme, the substrate of the enzyme, or any combination thereof.

A polynucleotide may be "introduced" into a fungal cell by any means known to those of skill in the art, including transfection, transformation or transduction, transposable element, electroporation, particle bombardment, infection and the like. The introduced polynucleotide may be maintained in the cell stably if it is incorporated into a non-chromosomal autonomous replicon or integrated into the fungal chromosome. Alternatively, the introduced polynucleotide may be present on an extra-chromosomal non-replicating vector and be transiently expressed or transiently active.

As used herein, the term "IPMD1" means a gene encoding 3-Isopropylmalate dehydratase activity, referring to an enzyme that catalyses the interconversion of 2-Isopropylmalate and $H_2O$ with 3-Isopropylmalate, and may also refer to the gene product.

As used herein, the terms "3-Isopropylmalate dehydratase" (EC 4.2.1.33), "α-isopropylmalate isomerase" and "3-Isopropylmalate dehydratase polypeptide" are synonymous with "the IPMD1 gene product" and refer to an enzyme that catalyses the interconversion of 2-Isopropylmalate and $H_2O$ with 3-Isopropylmalate.

As used herein, the term "knockout" or "gene disruption" refers to the creation of organisms carrying a null mutation (a mutation in which there is no active gene product), a partial null mutation or mutations, or an alteration or alterations in gene regulation by interrupting a DNA sequence through insertion of a foreign piece of DNA. Usually the foreign DNA encodes a selectable marker.

As used herein, the term "LB agar" means Luria's Broth agar.

The term "method of screening" means that the method is suitable, and is typically used, for testing for a particular property or effect in a large number of compounds. Typically, more than one compound is tested simultaneously (as in a 96-well microtitre plate), and preferably significant portions of the procedure can be automated. "Method of screening" also refers to the determination of a set of different properties or effects of one compound simultaneously.

As used herein, the term "mRNA" means messenger ribonucleic acid.

As used herein, the term "mutant form" of a gene refers to a gene which has been altered, either naturally or artificially, changing the base sequence of the gene. The change in the base sequence may be of several different types, including changes of one or more bases for different bases, deletions, and/or insertions, such as by a transposon. By contrast, a normal form of a gene (wild type) is a form commonly found in natural populations of an organism. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the strain having that gene, while a mutant form of a gene suitable for use in these methods does provide such a growth conditional phenotype.

As used herein, the term "Ni" refers to nickel.

As used herein, the term "Ni—NTA" refers to nickel sepharose.

As used herein, a "normal" form of a gene (wild type) is a form commonly found in natural populations of an organism. Commonly a single form of a gene will predominate in natural populations. In general, such a gene is suitable as a normal form of a gene, however, other forms which provide similar functional characteristics may also be used as a normal gene. In particular, a normal form of a gene does not confer a growth conditional phenotype on the strain having that gene, while a mutant form of a gene suitable for use in these methods does provide such a growth conditional phenotype.

As used herein, the term "one form" of a gene is synonymous with the term "gene", and a "different form" of a gene refers to a gene that has greater than 49% sequence identity and less than 100% sequence identity with said first form.

As used herein, the term "pathogenicity" refers to a capability of causing disease. The term is applied to parasitic microorganisms in relation to their hosts.

As used herein, the term "PCR" means polymerase chain reaction.

The "percent (%) sequence identity" between two polynucleotide or two polypeptide sequences is determined according to the either the BLAST program (Basic Local Alignment Search Tool; (Altschul, S. F., W. Gish, et al. (1990) J Mol Biol 215: 403–10 (PMID: 2231712)) at the National Center for Biotechnology or using Smith Waterman Alignment (Smith, T. F. and M. S. Waterman (1981) J Mol Biol 147: 195–7 (PMID: 7265238)) as incorporated into GeneMatcher Plus™. It is understood that for the purposes of determining sequence identity when comparing a DNA sequence to an RNA sequence, a thymine nucleotide is equivalent to a uracil nucleotide.

By "polypeptide" is meant a chain of at least two amino acids joined by peptide bonds. The chain may be linear, branched, circular or combinations thereof. Preferably, polypeptides are from about 10 to about 1000 amino acids in length, more preferably 10–50 amino acids in length. The polypeptides may contain amino acid analogs and other modifications, including, but not limited to glycosylated or phosphorylated residues.

As used herein, the term "proliferation" is synonymous to the term "growth".

As used herein, the term "reverse transcriptase-PCR" means reverse transcription-polymerase chain reaction.

As used herein, the term "RNA" means ribonucleic acid.

As used herein, "semi-permissive conditions" are conditions in which the relevant culture parameter for a particular growth conditional phenotype is intermediate between permissive conditions and non-permissive conditions. Consequently, in semi-permissive conditions an organism having a growth conditional phenotype will exhibit growth rates intermediate between those shown in permissive conditions and non-permissive conditions. In general, such intermediate growth rate may be due to a mutant cellular component which is partially functional under semi-permissive conditions, essentially fully functional under permissive conditions, and is non-functional or has very low function under non-permissive conditions, where the level of function of that component is related to the growth rate of the organism. An intermediate growth rate may also be a result of a nutrient substance or substances that are present in amounts not sufficient for optimal growth rates to be achieved.

"Sensitivity phenotype" refers to a phenotype that exhibits either hypersensitivity or hyposensitivity.

The term "specific binding" refers to an interaction between 3-Isopropylmalate dehydratase and a molecule or compound, wherein the interaction is dependent upon the primary amino acid sequence and/or the conformation of 3-Isopropylmalate dehydratase.

As used herein, the term "TLC" means thin layer chromatography.

"Transform", as used herein, refers to the introduction of a polynucleotide (single or double stranded DNA, RNA, or a combination thereof) into a living cell by any means. Transformation may be accomplished by a variety of methods, including, but not limited to, electroporation, polyethylene glycol mediated uptake, particle bombardment, agrotransformation, and the like. This process may result in transient or stable expression of the transformed polynucleotide. By "stably transformed" is meant that the sequence of interest is integrated into a replicon in the cell, such as a chromosome or episome. Transformed cells encompass not only the end product of a transformation process, but also the progeny thereof which retain the polynucleotide of interest.

For the purposes of the invention, "transgenic" refers to any cell, spore, tissue or part, that contains all or part of at least one recombinant polynucleotide. In many cases, all or part of the recombinant polynucleotide is stably integrated into a chromosome or stable extra-chromosomal element, so that it is passed on to successive generations.

As used herein, the term "transposase" refers to an enzyme that catalyzes transposition. Preferred transposons are described in WO 00/55346, PCT/US00/07317, and U.S. Ser. No. 09/658,859.

As used herein, the term "transposition" refers to a complex genetic rearrangement process involving the movement or copying of a polynucleotide (transposon) from one location and insertion into another, often within or between a genome or genomes, or DNA constructs such as plasmids, bacmids, and cosmids.

As used herein, the term "transposon" (also known as a "transposable element", "transposable genetic element", "mobile element", or "jumping gene") refers to a mobile DNA element such as those, for example, described in WO 00/55346, PCT/US00/07317, and U.S. Pat. No. 09/658,859. Transposons can disrupt gene expression or cause deletions and inversions, and hence affect both the genotype and phenotype of the organisms concerned. The mobility of transposable elements has long been used in genetic manipulation, to introduce genes or other information into the genome of certain model systems.

As used herein, the term "Tween 20" means sorbitan mono-9-octadecenoate poly(oxy-1,1-ethanediyl).

As used in this disclosure, the term "viability" of an organism refers to the ability of an organism to demonstrate growth under conditions appropriate for said organism, or to demonstrate an active cellular function. Some examples of active cellular functions include respiration as measured by gas evolution, secretion of proteins and/or other compounds, dye exclusion, mobility, dye oxidation, dye reduction, pigment production, changes in medium acidity, and the like.

The present inventors have discovered that disruption of the IPMD1 gene and/or gene product inhibits the pathogenicity of *Magnaporthe grisea*. Thus, the inventors are the first to demonstrate that 3-Isopropylmalate dehydratase is a target for antibiotics, preferably antifungals.

Accordingly, the invention provides methods for identifying compounds that inhibit IPMD1 gene expression or biological activity of its gene product(s). Such methods include ligand binding assays, assays for enzyme activity, cell-based assays, and assays for IPMD1 gene expression. Any compound that is a ligand for 3-Isopropylmalate dehydratase may have antibiotic activity. For the purposes of the invention, "ligand" refers to a molecule that will bind to a site on a polypeptide. The compounds identified by the methods of the invention are useful as antibiotics.

Thus, in one embodiment, the invention provides a method for identifying a test compound as a candidate for an antibiotic, comprising:

a) contacting a 3-Isopropylmalate dehydratase polypeptide with a test compound; and b) detecting the presence or absence of binding between said test compound and said 3-Isopropylmalate dehydratase polypeptide;

wherein binding indicates that said test compound is a candidate for an antibiotic.

The 3-Isopropylmalate dehydratase protein may have the amino acid sequence of a naturally occurring 3-Isopropylmalate dehydratase found in a fungus, animal, plant, or microorganism, or may have an amino acid sequence derived from a naturally occurring sequence. Preferably the 3-Isopropylmalate dehydratase is a fungal 3-Isopropylmalate dehydratase. The cDNA (SEQ ID NO: 1) encoding the 3-Isopropylmalate dehydratase protein, the genomic DNA (SEQ ID NO: 2) encoding the *M. grisea* protein, and the polypeptide (SEQ ID NO: 3) can be found herein.

In one aspect, the invention also provides for a polypeptide consisting essentially of SEQ ID NO: 3. For the purposes of the invention, a polypeptide consisting essentially of SEQ ID NO: 3 has at least 80% sequence identity with SEQ ID NO: 3 and catalyses the interconversion of 2-Isopropylmalate and $H_2O$ with 3-Isopropylmalate with at least 10% of the activity of SEQ ID NO: 3. Preferably, the polypeptide consisting essentially of SEQ ID NO: 3 has at least 85% sequence identity with SEQ ID NO: 3, more preferably the sequence identity is at least 90%, most preferably the sequence identity is at least 95% or 97 or 99%, or any integer from 80–100% sequence identity in ascending order. And, preferably, the polypeptide consisting essentially of SEQ ID NO: 3 has at least 25%, at least 50%, at least 75% or at least 90% of the activity of *M. grisea* 3-Isopropylmalate dehydratase, or any integer from 60–100% activity in ascending order.

By "fungal 3-Isopropylmalate dehydratase" is meant an enzyme that can be found in at least one fungus, and which catalyzes the interconversion of 2-Isopropylmalate and $H_2O$ with 3-Isopropylmalate. The 3-Isopropylmalate dehydratase may be from any of the fungi, including ascomycota, zygomycota, basidiomycota, chytridiomycota, and lichens.

In one embodiment, the 3-Isopropylmalate dehydratase is a Magnaporthe 3-Isopropylmalate dehydratase. Magnaporthe species include, but are not limited to, *Magnaporthe rhizophila, Magnaporthe salvinii, Magnaporthe grisea* and *Magnaporthe poae* and the imperfect states of Magnaporthe in the genus Pyricularia. Preferably, the Magnaporthe 3-Isopropylmalate dehydratase is from *Magnaporthe grisea.*

In various embodiments, the 3-Isopropylmalate dehydratase can be from Powdery Scab (*Spongospora subterranea*), Grey Mould (*Botrytis cinerea*), White Rot (*Armillaria mellea*), Heartrot Fungus (*Ganoderma adspersum*), Brown-Rot (*Piptoporus betulinus*), Corn Smut (*Ustilago maydis*), Heartrot (*Polyporus squamosus*), Gray Leaf Spot (*Cercospora zeae-maydis*), Honey Fungus (*Armillaria gallica*), Root rot (*Armillaria luteobubalina*), Shoestring Rot (*Armillaria ostoyae*), Banana Anthracnose Fungus (*Colletotrichum musae*), Apple-rotting Fungus (*Monilinia fructigena*), Apple-rotting Fungus (*Penicillium expansum*), Clubroot Disease (*Plasmodiophora brassicae*), Potato Blight (*Phytophthora infestans*), Root pathogen (*Heterobasidion annosum*), Take-all Fungus (*Gaeumannomyces graminis*), Dutch Elm Disease (*Ophiostoma ulmi*), Bean Rust (*Uromyces appendiculatus*), Northern Leaf Spot (*Cochliobolus carbonum*), Milo Disease (*Periconia circinata*), Southern Corn Blight (*Cochliobolus heterostrophus*), Leaf Spot (*Cochliobolus lunata*), Brown Stripe (*Cochliobolus stenospilus*), Panama disease (*Fusarium oxysporum*), Wheat Head Scab Fungus (*Fusarium graminearum*), Cereal Foot Rot (*Fusarium culmorum*), Potato Black Scurf (*Rhizoctonia solani*), Wheat Black Stem Rust (*Puccinia graminis*), White mold (*Sclerotinia sclerotiorum*), and the like.

Fragments of a 3-Isopropylmalate dehydratase polypeptide may be used in the methods of the invention, preferably if the fragments include an intact or nearly intact epitope that occurs on the biologically active wildtype 3-Isopropylmalate dehydratase. The fragments comprise at least 10 consecutive amino acids of a 3-Isopropylmalate dehydratase. Preferably, the fragment comprises at least 15, 20, 25, 30, 35, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, or at least 770 consecutive amino acids residues of a 3-Isopropylmalate dehydratase. In one embodiment, the fragment is from a Magnaporthe 3-Isopropylmalate dehydratase. Preferably, the fragment contains an amino acid sequence conserved among fungal 3-Isopropylmalate dehydratases.

Polypeptides having at least 50% sequence identity with a fungal 3-Isopropylmalate dehydratase are also useful in the methods of the invention. Preferably, the sequence identity is at least 60%, more preferably the sequence identity is at least 70%, most preferably the sequence identity is at least 80% or 90 or 95 or 99%, or any integer from 60–100% sequence identity in ascending order.

In addition, it is preferred that the polypeptide has at least 10% of the activity of a fungal 3-Isopropylmalate dehydratase. More preferably, the polypeptide has at least 25%, at least 50%, at least 75% or at least 90% of the activity of a fungal 3-Isopropylmalate dehydratase. Most preferably, the polypeptide has at least 10%, at least 25%, at least 50%, at least 75% or at least 90% of the activity of the *M. grisea* 3-Isopropylmalate dehydratase protein.

Thus, in another embodiment, the invention provides a method for identifying a test compound as a candidate for a fungicide, comprising:

a) contacting a test compound with at least one polypeptide selected from the group consisting of: a polypeptide having at least ten consecutive amino acids of a fungal 3-Isopropylmalate dehydratase; a polypeptide having at least 50% sequence identity with a fungal 3-Isopropylmalate dehydratase; and a polypeptide having at least 10% of the activity of a fungal 3-Isopropylmalate dehydratase; and b) detecting the presence and/or absence of binding between said test compound and said polypeptide; wherein binding indicates that said test compound is a candidate for an antibiotic.

Any technique for detecting the binding of a ligand to its target may be used in the methods of the invention. For example, the ligand and target are combined in a buffer. Many methods for detecting the binding of a ligand to its target are known in the art, and include, but are not limited to the detection of an immobilized ligand-target complex or the detection of a change in the properties of a target when it is bound to a ligand. For example, in one embodiment, an array of immobilized candidate ligands is provided. The immobilized ligands are contacted with a 3-Isopropylmalate dehydratase protein or a fragment or variant thereof, the unbound protein is removed and the bound 3-Isopropylmalate dehydratase is detected. In a preferred embodiment, bound 3-Isopropylmalate dehydratase is detected using a labeled binding partner, such as a labeled antibody. In a variation of this assay, 3-Isopropylmalate dehydratase is labeled prior to contacting the immobilized candidate ligands. Preferred labels include fluorescent or radioactive moieties. Preferred detection methods include fluorescence correlation spectroscopy (FCS) and FCS-related confocal nanofluorimetric methods.

Once a compound is identified as a candidate for an antibiotic, it can be tested for the ability to inhibit 3-Isopropylmalate dehydratase enzymatic activity. The compounds can be tested using either in vitro or cell based assays. Alternatively, a compound can be tested by applying it directly to a fungus or fungal cell, or expressing it therein, and monitoring the fungus or fungal cell for changes or decreases in growth, development, viability, pathogenicity, or alterations in gene expression. Thus, in one embodiment, the invention provides a method for determining whether a compound identified as an antibiotic candidate by an above method has antifungal activity, further comprising: contacting a fungus or fungal cells with said antifungal candidate and detecting a decrease in the growth, viability, or pathogenicity of said fungus or fungal cells.

By decrease in growth, is meant that the antifungal candidate causes at least a 10% decrease in the growth of the fungus or fungal cells, as compared to the growth of the fungus or fungal cells in the absence of the antifungal candidate. By a decrease in viability is meant that at least 20% of the fungal cells, or portion of the fungus contacted with the antifungal candidate are nonviable. Preferably, the growth or viability will be decreased by at least 40%. More preferably, the growth or viability will be decreased by at least 50%, 75% or at least 90% or more. Methods for measuring fungal growth and cell viability are known to those skilled in the art. By decrease in pathogenicity, is meant that the antifungal candidate causes at least a 10% decrease in the disease caused by contact of the fungal pathogen with its host, as compared to the disease caused in the absence of the antifungal candidate. Preferably, the disease will be decreased by at least 40%. More preferably, the disease will be decreased by at least 50%, 75% or at least 90% or more. Methods for measuring fungal disease are well known to those skilled in the art, and include such metrics as lesion formation, lesion size, sporulation, respiratory failure, and/or death.

The ability of a compound to inhibit 3-Isopropylmalate dehydratase activity can be detected using in vitro enzymatic assays in which the disappearance of a substrate or the appearance of a product is directly or indirectly detected. 3-Isopropylmalate dehydratase catalyzes the irreversible or reversible reaction 2-Isopropylmalate and $H_2O$=3-Isopropylmalate (see FIG. 1). Methods for detection of 2-Isopropylmalate, $H_2O$, and/or 3-Isopropylmalate, include spectrophotometry, mass spectroscopy, thin layer chromatography (TLC) and reverse phase HPLC.

Thus, the invention provides a method for identifying a test compound as a candidate for an antibiotic, comprising:

a) contacting 2-Isopropylmalate and $H_2O$ with a 3-Isopropylmalate dehydratase;

b) contacting 2-Isopropylmalate and $H_2O$ with 3-Isopropylmalate dehydratase and said test compound; and c) determining the change in concentration for at least one of the following: 2-Isopropylmalate, $H_2O$, and/or 3-Isopropylmalate, wherein a change in concentration for any of the above substances indicates that said test compound is a candidate for an antibiotic.

An additional method is provided by the invention for identifying a test compound as a candidate for an antibiotic, comprising:

a) contacting 3-Isopropylmalate with a 3-Isopropylmalate dehydratase;

b) contacting 3-Isopropylmalate with a 3-Isopropylmalate dehydratase and a test compound; and c) determining the change in concentration for at least one of the following: 2-Isopropylmalate, $H_2O$, and/or 3-Isopropylmalate, wherein a change in concentration for any of the above substances indicates that said test compound is a candidate for an antibiotic.

Enzymatically active fragments of a fungal 3-Isopropylmalate dehydratase are also useful in the methods of the invention. For example, an enzymatically active polypeptide comprising at least 100 consecutive amino acid residues of a fungal 3-Isopropylmalate dehydratase may be used in the methods of the invention. In addition, an enzymatically active polypeptide having at least 50%, 60%, 70%, 80%, 90%, 95% or at least 98% sequence identity with a fungal 3-Isopropylmalate dehydratase may be used in the methods of the invention. Most preferably, the polypeptide has at least 50% sequence identity with a fungal 3-Isopropylmalate dehydratase and at least 10%, 25%, 75% or at least 90% of the activity thereof.

Thus, the invention provides a method for identifying a test compound as a candidate for an antibiotic, comprising:

a) contacting 2-Isopropylmalate and $H_2O$ with a polypeptide selected from the group consisting of: a polypeptide having at least 50% sequence identity with a 3-Isopropylmalate dehydratase; a polypeptide having at least 50% sequence identity with a 3-Isopropylmalate dehydratase and having at least 10% of the activity thereof; and a polypeptide comprising at least 100 consecutive amino acids of a 3-Isopropylmalate dehydratase;

b) contacting 2-Isopropylmalate and $H_20$ with said polypeptide and a test compound; and c) determining the change in concentration for at least one of the following: 2-Isopropylmalate, $H_2O$, and/or 3-Isopropylmalate; wherein a change in concentration for any of the above substances indicates that said test compound is a candidate for an antibiotic.

An additional method is provided by the invention for identifying a test compound as a candidate for an antibiotic, comprising:

a) contacting 3-Isopropylmalate with a polypeptide selected from the group consisting of: a polypeptide having at least 50% sequence identity with a 3-Isopropylmalate dehydratase; a polypeptide having at least 50% sequence identity with a 3-Isopropylmalate dehydratase and at least 10% of the activity thereof; and a polypeptide comprising at least 100 consecutive amino acids of a 3-Isopropylmalate dehydratase;

b) contacting 3-Isopropylmalate, with said polypeptide and a test compound; and c) determining the change in concentration for at least one of the following, 2-Isopropylmalate, $H_2O$, and/or 3-Isopropylmalate;

wherein a change in concentration for any of the above substances indicates that said test compound is a candidate for an antibiotic.

For the in vitro enzymatic assays, 3-Isopropylmalate dehydratase protein and derivatives thereof may be purified from a fungus or may be recombinantly produced in and purified from an archael, bacterial, fungal, or other eukaryotic cell culture. Preferably these proteins are produced using an *E. coli*, yeast, or filamentous fungal expression system. Methods for the purification of 3-Isopropylmalate dehydratase may be described in (Bigelis and Umbarger (1975) J Biol Chem 250: 4315–21 (PMID: 1126953); Kohlhaw (1988) Meth Enzymol 166: 423–9 (PMID: 3071717)). Other methods for the purification of 3-Isopropylmalate dehydratase proteins and polypeptides are known to those skilled in the art.

As an alternative to in vitro assays, the invention also provides cell based assays. In one embodiment, the invention provides a method for identifying a test compound as a candidate for an antibiotic, comprising:

a) measuring the expression of a 3-Isopropylmalate dehydratase in a cell, cells, tissue, or an organism in the absence of a test compound;

b) contacting said cell, cells, tissue, or organism with said test compound and measuring the expression of said 3-Isopropylmalate dehydratase in said cell, cells, tissue, or organism; and c) comparing the expression of 3-Isopropylmalate dehydratase in steps (a) and (b);

wherein a lower expression in the presence of said test compound indicates that said compound is a candidate for an antibiotic.

Expression of 3-Isopropylmalate dehydratase can be measured by detecting the IPMD1 primary transcript or mRNA, 3-Isopropylmalate dehydratase polypeptide, or 3-Isopropylmalate dehydratase enzymatic active RNA and proteins are known to those skilled in the art. See, for example, *Current Protocols in Molecular Biology* Ausubel et al., eds., Greene Publishing and Wiley-Interscience, New York, 1995. The method of detection is not critical to the invention. Methods for detecting IPMD1 RNA include, but are not limited to amplification assays such as quantitative reverse transcriptase-PCR, and/or hybridization assays such as Northern analysis, dot blots, slot blots, in-situ hybridization, transcriptional fusions using an IPMD1 promoter fused to a reporter gene, DNA assays, and microarray assays.

Methods for detecting protein expression include, but are not limited to, immunodetection methods such as Western blots, ELISA assays, polyacrylamide gel electrophoresis, mass spectroscopy, and enzymatic assays. Also, any reporter gene system may be used to detect IPMD1 protein expression. For detection using gene reporter systems, a polynucleotide encoding a reporter protein is fused in frame with IPMD1, so as to produce a chimeric polypeptide. Methods for using reporter systems are known to those skilled in the art.

Chemicals, compounds or compositions identified by the above methods as modulators, preferably inhibitors, of IPMD1 expression or activity can then be used to control fungal growth. Diseases such as rusts, mildews, and blights spread rapidly once established. Fungicides are thus routinely applied to growing and stored crops as a preventive measure, generally as foliar sprays or seed dressings. For example, compounds that inhibit fungal growth can be applied to a fungus or expressed in a fungus, in order to prevent fungal growth. Thus, the invention provides a method for inhibiting fungal growth, comprising contacting a fungus with a compound identified by the methods of the invention as having antifungal activity.

Antifungals and antifungal inhibitor candidates identified by the methods of the invention can be used to control the growth of undesired fungi, including ascomycota, zygomycota, basidiomycota, chytridiomycota, and lichens.

Examples of undesired fungi include, but are not limited to Powdery Scab (*Spongospora subterranea*), Grey Mould (*Botrytis cinerea*), White Rot (*Armillaria mellea*), Heartrot Fungus (*Ganoderma adspersum*), Brown-Rot (*Piptoporus betulinus*), Corn Smut (*Ustilago maydis*), Heartrot (*Polyporus squamosus*), Gray Leaf Spot (*Cercospora zeae-maydis*), Honey Fungus (*Armillaria gallica*), Root rot (*Armillaria luteobubalina*), Shoestring Rot (*Armillaria ostoyae*), Banana Anthracnose Fungus (*Colletotrichum musae*), Apple-rotting Fungus (*Monilinia fructigena*), Apple-rotting Fungus (*Penicillium expansum*), Clubroot Disease (*Plasmodiophora brassicae*), Potato Blight (*Phytophthora infestans*), Root pathogen (*Heterobasidion annosum*), Take-all Fungus (*Gaeumannomyces graminis*), Dutch Elm Disease (*Ophiostoma ulmi*), Bean Rust (*Uromyces appendiculatus*), Northern Leaf Spot (*Cochliobolus carbonum*), Milo Disease (*Periconia circinata*), Southern Corn Blight (*Cochliobolus heterostrophus*), Leaf Spot (*Cochliobolus lunata*), Brown Stripe (*Cochliobolus stenospilus*), Panama disease (*Fusarium oxysporum*), Wheat Head Scab Fungus (*Fusarium graminearum*), Cereal Foot Rot (*Fusarium culmorum*), Potato Black Scurf (*Rhizoctonia solani*), Wheat Black Stem Rust (*Puccinia graminis*), White mold (*Sclerotinia sclerotiorum*), diseases of animals such as infections of lungs, blood, brain, skin, scalp, nails or other tissues (*Aspergillus fumigatus* Aspergillus sp. Fusraium sp., Trichophyton sp., Epidermophyton sp., and Microsporum sp., and the like).

Also provided is a method of screening for an antibiotic by determining whether a test compound is active against the gene identified (SEQ ID NO: 1 or SEQ ID NO: 2), its gene product (SEQ ID NO: 3), or the biochemical pathway or pathways it functions on.

In one particular embodiment, the method is performed by providing an organism having a first form of the gene corresponding to either SEQ ID NO: 1 or SEQ ID NO: 2, either a normal form, a mutant form, a homologue, or a heterologous IPMD1 gene that performs a similar function as IPMD1. The first form of IPMD1 may or may not confer a growth conditional phenotype, i.e., a L-leucine requiring phenotype, and/or a hypersensitivity or hyposensitivity phenotype on the organism having that altered form. In one particular embodiment a mutant form contains a transposon insertion. A comparison organism having a second form of an IPMD1, different from the first form of the gene is also provided, and the two organisms are separately contacted with a test compound. The growth of the two organisms in the presence of the test compound is then compared.

Thus, in one embodiment, the invention provides a method for identifying a test compound as a candidate for an antibiotic, comprising:

a) providing cells having one form of a 3-Isopropylmalate dehydratase gene, and providing comparison cells having a different form of a 3-Isopropylmalate dehydratase gene; and b) contacting said cells and said comparison cells with a test compound and determining the growth of said cells and said comparison cells in the presence of the test compound, wherein a difference in growth between said cells and said comparison cells in the presence of said test compound indicates that said test compound is a candidate for an antibiotic.

It is recognized in the art that the optional determination of the growth of said first organism and said comparison second organism in the absence of any test compounds may be performed to control for any inherent differences in growth as a result of the different genes. It is also recognized that any combination of two different forms of an IPMD1 gene, including normal genes, mutant genes, homologues, and functional homologues may be used in this method. Growth and/or proliferation of an organism is measured by methods well known in the art such as optical density measurements, and the like. In a preferred embodiment the organism is *Magnaporthe grisea*.

Conditional lethal mutants may identify particular biochemical and/or genetic pathways given that at least one identified target gene is present in that pathway. Knowledge of these pathways allows for the screening of test compounds as candidates for antibiotics as inhibitors of the substrates, products and enzymes of the pathway. Pathways known in the art may be found at the Kyoto Encyclopedia of Genes and Genomes and in standard biochemistry texts (Lehninger, A., D. Nelson, et al. (1993) *Principles of Biochemistry*. New York, Worth Publishers).

Thus, in one embodiment, the invention provides a method for screening for test compounds acting against the biochemical and/or genetic pathway or pathways in which IPMD1 functions, comprising:

a) providing cells having one form of a gene in the L-leucine biochemical and/or genetic pathway and providing comparison cells having a different form of said gene;

b) contacting said cells and said comparison cells with a test compound; and c) determining the growth of said cells and said comparison cells in the presence of said test compound;

wherein a difference in growth between said cells and said comparison cells in the presence of said test compound indicates that said test compound is a candidate for an antibiotic.

The use of multi-well plates for screening is a format that readily accommodates multiple different assays to characterize various compounds, concentrations of compounds, and fungal strains in varying combinations and formats. Certain testing parameters for the screening method can significantly affect the identification of growth inhibitors, and thus can be manipulated to optimize screening efficiency and/or reliability. Notable among these factors are variable sensitivities of different mutants, increasing hypersensitivity with increasingly less permissive conditions, an apparent increase in hypersensitivity with increasing compound concentration, and other factors known to those in the art.

Conditional lethal mutants may identify particular biochemical and/or genetic pathways given that at least one identified target gene is present in that pathway. Knowledge of these pathways allows for the screening of test compounds as candidates for antibiotics. Pathways known in the art may be found at the Kyoto Encyclopedia of Genes and Genomes and in standard biochemistry texts (Lehninger, A., D. Nelson, et al. (1993) *Principles of Biochemistry*. New York, Worth Publishers).

Thus, in one embodiment, the invention provides a method for screening for test compounds acting against the biochemical and/or genetic pathway or pathways in which IPMD1 functions, comprising:

(a) providing paired growth media comprising a first medium and a second medium, wherein said second medium contains a higher level of L-leucine than said first medium;

(b) contacting an organism with a test compound;

(c) inoculating said first and said second media with said organism; and (d) determining the growth of said organism;

wherein a difference in growth of the organism between said first and said second media indicates that said test compound is a candidate for an antibiotic.

It is recognized in the art that determination of the growth of said organism in the paired media in the absence of any test compounds may be performed to control for any inherent differences in growth as a result of the different media. Growth and/or proliferation of an organism is measured by methods well known in the art such as optical density measurements, and the like. In a preferred embodiment, the organism is *Magnaporthe grisea.*

EXPERIMENTAL

Example 1

Construction of Plasmids with a Transposon Containing a Selectable Marker

Construction of Sif transposon: Sif was constructed using the GPS3 vector from the GPS-M mutagenesis system from New England Biolabs, Inc. (Beverly, Mass.) as a backbone. This system is based on the bacterial transposon Tn7. The following manipulations were done to GPS3 according to Sambrook et al. (1989) *Molecular Cloning, a Laboratory Manual*, Cold Spring Harbor Laboratory Press. The kanamycin resistance gene (npt) contained between the Tn7 arms was removed by EcoRV digestion. The bacterial hygromycin B phosphotransferase (hph) gene (Gritz and Davies (1983) Gene 25: 179–88 (PMID: 6319235)) under control of the *Aspergillus nidulans* trpC promoter and terminator (Mullaney et al. (1985) Mol Gen Genet 199: 37–45 (PMID: 3158796)) was cloned by a HpaI/EcoRV blunt ligation into the Tn7 arms of the GPS3 vector yielding pSif1. Excision of the ampicillin resistance gene (bla) from pSif1 was achieved by cutting pSif1 with XmnI and BglI followed by a T4 DNA polymerase treatment to remove the 3' overhangs left by the BglI digestion and religation of the plasmid to yield pSif. Top 10F' electrocompetent *E. coli* cells (Invitrogen) were transformed with ligation mixture according to manufacturer's recommendations. Transformants containing the Sif transposon were selected on LB agar (Sambrook et al. (1989) *Molecular Cloning, a Laboratory Manual*, Cold Spring Harbor Laboratory Press.) containing 50 ug/ml of hygromycin B (Sigma Chem. Co., St. Louis, Mo.).

Example 2

Construction of a Fungal Cosmid Library

Cosmid libraries were constructed in the pcosKA5 vector (Hamer et al. (200 1) Proc Natl Acad Sci USA 98: 5110–15 (PMID: 11296265)) as described in Sambrook et al. (1989) *Molecular Cloning, a Laboratory Manual*, Cold Spring Harbor Laboratory Press. Cosmid libraries were quality checked by pulsed-field gel electrophoresis, restriction digestion analysis, and PCR identification of single genes.

Example 3

Construction of Cosmids with Transposon Insertion into Fungal Genes

Sif Transposition into a Cosmid: Transposition of Sif into the cosmid framework was carried out as described by the GPS-M mutagenesis system (New England Biolabs, Inc.). Briefly, 2 ul of the 10× GPS buffer, 70 ng of supercoiled pSIF, 8–12 $\mu$g of target cosmid DNA were mixed and taken to a final volume of 20 ul with water. 1 ul of transposase (TnsABC) was added to the reaction and incubated for 10 minutes at 37° C. to allow the assembly reaction to happen. After the assembly reaction 1 ul of start solution was added to the tube, mixed well and incubated for 1 hour at 37° C. followed by heat inactivation of the proteins at 75° C. for 10 min. Destruction of the remaining untransposed pSif was done by PISceI digestion at 37° C. for 2 hours followed by 10 min incubation at 75° C. to inactivate the proteins. Transformation of Top10F' electrocompetent cells (Invitrogen) was done according to manufacturers recommendations. Sif-containing cosmid transformants were selected by growth on LB agar plates containing 50 ug/ml of hygromycin B (Sigma Chem. Co.) and 100 ug/ml of Ampicillin (Sigma Chem. Co.).

Example 4

High Throughput Preparation and Verification of Transposon Insertion into the *M. grisea* IPMD1 Gene

*E. coli* strains containing cosmids with transposon insertions were picked to 96 well growth blocks (Beckman Co.) containing 1.5 ml of TB (Terrific Broth, Sambrook et al. (1989) *Molecular Cloning, a Laboratory Manual*, Cold Spring Harbor Laboratory Press) supplemented with 50 ug/ml of ampicillin. Blocks were incubated with shaking at 37 C. overnight. *E. coli* cells were pelleted by centrifugation and cosmids were isolated by a modified alkaline lysis method (Marra et al. (1997) Genome Res 7: 1072–84 (PMID: 9371743)). DNA quality was checked by electrophoresis on agarose gels. Cosmids were sequenced using primers from the ends of each transposon and commercial dideoxy sequencing kits (Big Dye Terminators, Perkin Elmer Co.). Sequencing reactions were analyzed on an ABI377 DNA sequencer (Perkin Elmer Co.).

DNA sequences adjacent to the site of the insertion were collected and used to search DNA and protein databases using the BLAST algorithms (Altschul et al. (1997) Nucleic Acids Res 25: 3389–3402 (PMID: 9254694)). A single insertion of SIF into the *Magnaporthe grisea* IPMD1 gene was chosen for further analysis. This construct was designated cpgmra0014081f03 and it contains the SIF transposon approximately between amino acids 560 and 561 relative to the *Rhizomucor pusillus* homologue LeuA (total length: 755 amino acids, SWISS-PROT: P55251).

Example 5

Preparation of IPMD1 Cosmid DNA and Transformation of *Magnaporthe grisea*

Cosmid DNA from the IPMD1 transposon tagged cosmid clone was prepared using QIAGEN Plasmid Maxi Kit (QIAGEN), and digested by PI-PspI (New England Biolabs, Inc.). Fungal electro-transformation was performed essentially as described (Wu et al. (1997) MPMI 10: 700–708). Briefly, *M. grisea* strain Guy 11 was grown in complete liquid media (Talbot et al. (1993) Plant Cell 5: 1575–1590 (PMID: 8312740)) shaking at 120 rpm for 3 days at 25° C. in the dark. Mycelia was harvested and washed with sterile $H_2O$ and digested with 4 mg/ml beta-glucanase (InterSpex) for 4–6 hours to generate protoplasts. Protoplasts were collected by centrifugation and resuspended in 20% sucrose at the concentration of $2\times10^8$ protoplasts/ml. 50 ul protoplast suspension was mixed with 10–20 ug of the cosmid DNA and pulsed using Gene Pulser II (BioRad) set with the following parameters: resistance 200 ohm, capacitance 25 uF, voltage 0.6 kV. Transformed protoplasts were regenerated in complete agar media (CM, Talbot et al. (1993) Plant Cell 5: 1575–1590 (PMID: 8312740)) with the addition of 20% sucrose for one day, then overlayed with CM agar media containing hygromycin B (250 ug/ml) to select transformants. Transformants were screened for homologous recombination events in the target gene by PCR (Hamer et al. (2001) Proc Natl Acad Sci USA 98: 5110–15 (PMID: 11296265)). Two independent strains were identified and are hereby referred to as KO1–3 and KO1–7, respectively.

Example 6

Effect of Transposon Insertion on Magnaporthe Pathogenicity

Figure 2:
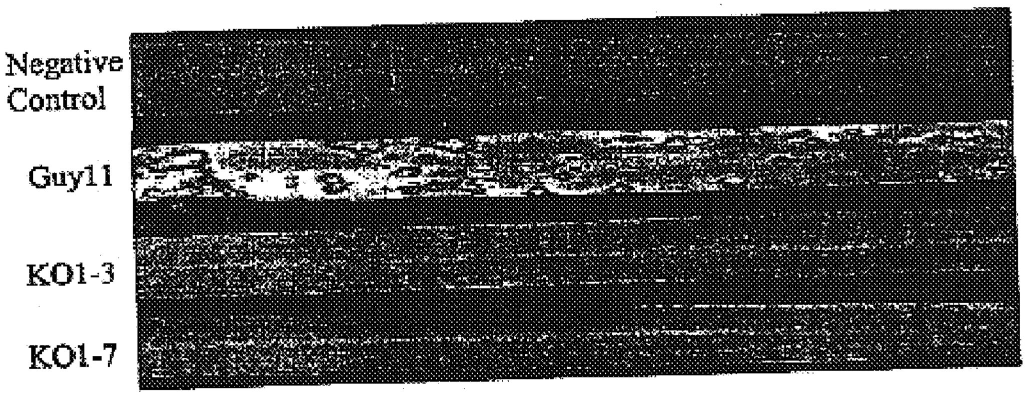
FIG. 2 shows a digital image showing the effect of IPMD1 gene disruption on *Magnaporthe grisea* pathogenicity using whole plant infection assays. Rice variety CO39 was inoculated with wild-type and the transposon insertion strains, KO1–3 and KO1–7. Leaf segments were imaged at five days post-inoculation.

The target fungal strains, KO1–3 and KO1–7, obtained in Example 5 and the wild type strain, Guy11, were subjected to a pathogenicity assay to observe infection over a 1-week period. Rice infection assays were performed using Indian rice cultivar CO39 essentially as described in Valent et al. ((1991) Genetics 127: 87–101 (PMID: 2016048)). All three strains were grown for spore production on complete agar media. Spores were harvested and the concentration of spores adjusted for whole plant inoculations. Two-week-old seedlings of cultivar CO39 were sprayed with 12 ml of conidial suspension ($5\times10^4$ conidia per ml in 0.01% Tween-20 (Polyoxyethylensorbitan monolaureate) solution). The inoculated plants were incubated in a dew chamber at 27° C. in the dark for 36 hours, and transferred to a growth chamber (27° C. 12 hours/21° C. 12 hours 70% humidity) for an additional 5.5 days. Leaf samples were taken at 3, 5, and 7 days post-inoculation and examined for signs of successful infection (i.e. lesions). FIG. 2 shows the effects of IPMD1 gene disruption on Magnaporthe infection at five days post-inoculation.

Example 7

Verification of IPMD1 Gene Function by Analysis of Nutritional Requirements

Figure 3:
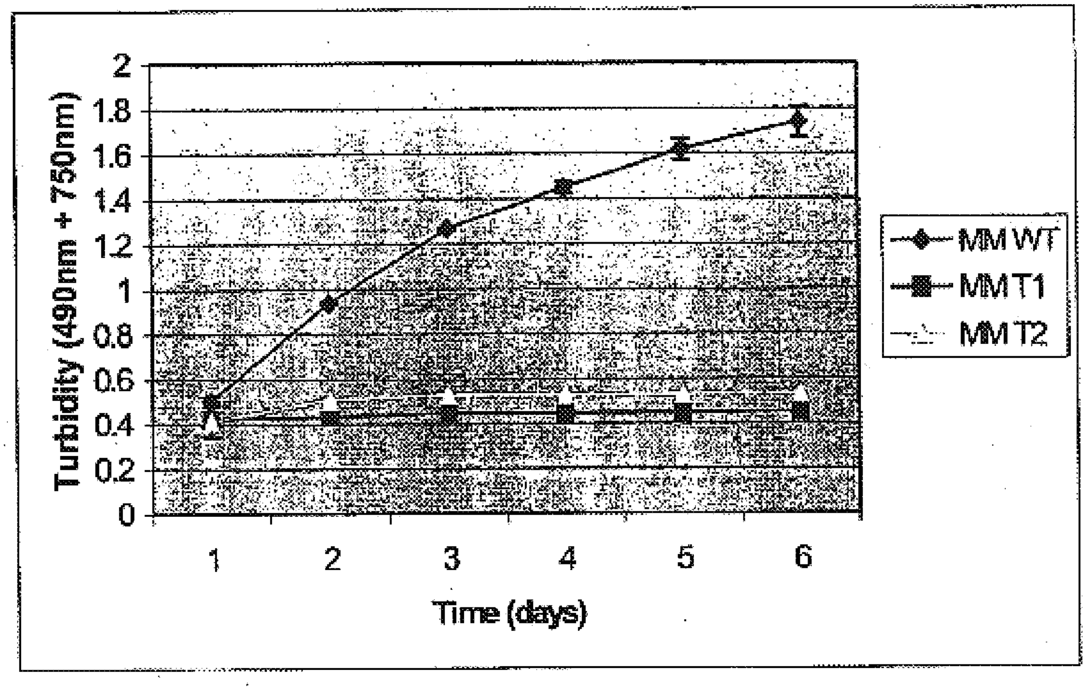
FIG. 3. Verification of Gene Function by Analysis of Nutritional Requirements. Wild-type and transposon insertion strains, KO1–3 and KO1–7, were grown in (A) minimal media and (B) minimal media with the addition of L-leucine, respectively. The x-axis shows time in days and the y-axis shows turbidity measured at 490 nanometers and 750 nanometers. The symbols represent wildtype (--◆--), transposon strain KO1–3 (T1) (--■--), and transposon strain KO1–7 (T2) (--▲--).
Figure 3:
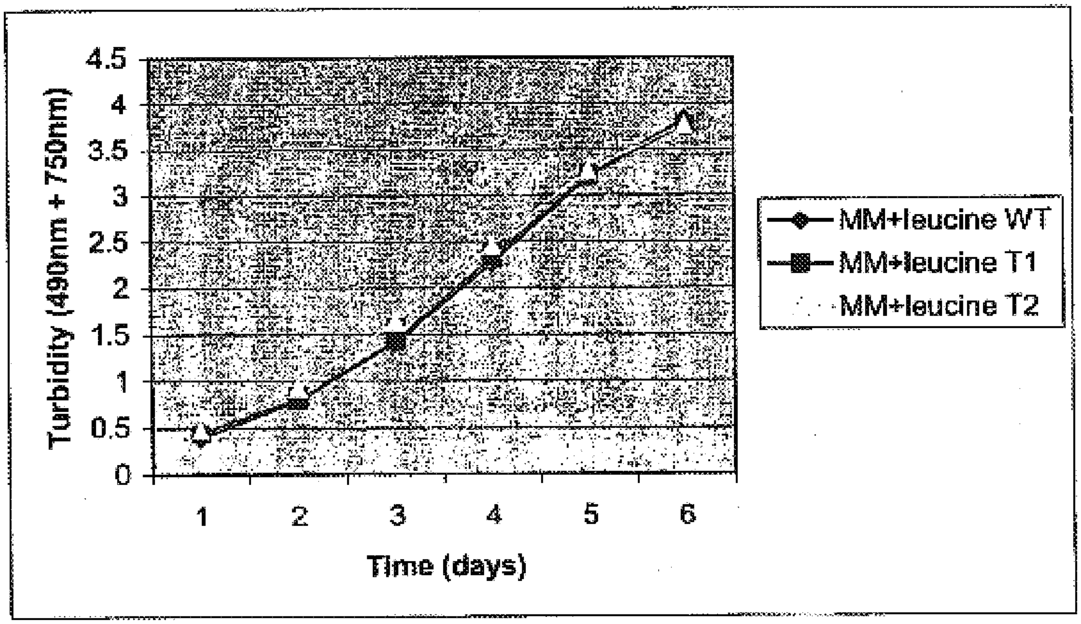

The fungal strains, KO1–3 and KO1–7, containing the IPMD1 disrupted gene obtained in Example 5 were analyzed for their nutritional requirement for L-leucine using the PM5 phenotype microarray from Biolog, Inc. (Hayward, Calif.). The PM5 plate tests for the auxotrophic requirement for 94 different metabolites. The inoculating fluid consists of 0.05% Phytagel, 0.03% Pluronic F68, 1% glucose, 23.5 mM $NaNO_3$, 6.7 mM KCl, 3.5 mM $Na_2SO_4$, 11 mM $KH_2PO_4$, 0.01% p-iodonitrotetrazolium violet, 0.1 mM $MgCl_2$, 1.0 mM $CaCl_2$ and trace elements. Final concentrations of trace elements are: 7.6 $\mu$M $ZnCl_2$, 2.5 $\mu$M $MnCl_2.4H_2O$, 1.8 $\mu$M $FeCl_2.4H_2O$, 0.71 $\mu$M $CoCl_2.6H_2O$, 0.64 $\mu$M $CuCl_2.2H_2O$, 0.62 $\mu$M $Na_2MoO_4$, 18 $\mu$M $H_3BO_3$. pH adjusted to 6.0 with NaOH. Spore for each strain were harvested into the inoculating fluid. The spore concentrations were adjusted to $2\times10^5$ spores/ml. 100 $\mu$l of spore suspension were deposited into each well of the microtiter plates. The plates were incubated at 25° C. for 7 days. Optical density (OD) measurements at 490 nm and 750 nm were taken daily. The $OD_{490}$ measures the extent of tetrazolium dye reduction and the level of growth, and $OD_{750}$ measures growth only. Turbidity=$OD_{490}$+$OD_{750}$. Data confirming the annotated gene function is presented as a graph of Turbidity vs. Time showing both the mutant fungi and the wild-type control in the absence (FIG. 3A) and presence (FIG. 3B) of L-leucine.

Example 8

Cloning and Expression Strategies, Extraction and Purification of 3-Isopropylmalate Dehydratase Protein The following protocol may be employed to obtain a purified 3-Isopropylmalate dehydratase protein.

Cloning and Expression Strategies:

An IPMD1 cDNA gene can be cloned into *E. coli* (pET vectors-Novagen), Baculovirus (Pharmingen) and Yeast (Invitrogen) expression vectors containing His/fusion protein tags, and the expression of recombinant protein can be evaluated by SDS-PAGE and Western blot analysis.

Extraction:

Extract recombinant protein from 250 ml cell pellet in 3 ml of extraction buffer by sonicating 6 times, with 6 sec pulses at 4° C. Centrifuge extract at 15000×g for 10 min and collect supernatant. Assess biological activity of the recombinant protein by activity assay.

Purification:

Purify recombinant protein by Ni—NTA affinity chromatography (Qiagen). Purification protocol: perform all steps at 4° C.:

Use 3 ml Ni-beads (Qiagen)

Equilibrate column with the buffer

Load protein extract

Wash with the equilibration buffer

Elute bound protein with 0.5 M imidazole

Example 9

Assays for Testing Binding of Test Compounds to 3-Isopropylmalate Dehydratase The following protocol may be employed to identify test compounds that bind to the 3-Isopropylmalate dehydratase protein.

- Purified full-length 3-Isopropylmalate dehydratase polypeptide with a His/fusion protein tag (Example 8) is bound to a HisGrab™ Nickel Coated Plate (Pierce, Rockford, Ill.) following manufacturer's instructions.
- Buffer conditions are optimized (e.g. ionic strength or pH, as may be described in Satyanarayana et al. ((1968B) J Bacteriol 96: 2018–24 (PMID: 5724970)) and/or Kohlhaw ((1988) Methods Enzymol 166: 423–9 (PMID: 3071717))) for binding of radiolabeled 2-Isopropylmalate (custom made PerkinElmer Life Sciences, Inc., Boston, Mass.) to the bound 3-Isopropylmalate dehydratase.
- Screening of test compounds is performed by adding test compound and 2-Isopropylmalate (custom made PerkinElmer Life Sciences, Inc., Boston, Mass.) to the wells of the HisGrab™ plate containing bound 3-Isopropylmalate dehydratase.

The wells are washed to remove excess labeled ligand and scintillation fluid (Scintiverse®, Fisher Scientific) is added to each well.

The plates are read in a microplate scintillation counter.

Candidate compounds are identified as wells with lower radioactivity as compared to control wells with no test compound added.

Additionally, a purified polypeptide comprising 10–50 amino acids from the *M. grisea* 3-Isopropylmalate dehydratase is screened in the same way. A polypeptide comprising 10–50 amino acids is generated by subcloning a portion of the IPMD1 gene into a protein expression vector that adds a His-Tag when expressed (see Example 8). Oligonucleotide primers are designed to amplify a portion of the IPMD1 gene using the polymerase chain reaction amplification method. The DNA fragment encoding a polypeptide of 10–50 amino acids is cloned into an expression vector, expressed in a host organism and purified as described in Example 8 above.

Test compounds that bind IPMD1 are further tested for antibiotic activity. *M. grisea* is grown as described for spore production on oatmeal agar media (Talbot et al. (1993) Plant Cell 5: 1575–1590 (PMID: 8312740)). Spores are harvested into minimal media (Talbot et al. (1993) Plant Cell 5: 1575–1590 (PMID: 8312740)) to a concentration of $2\times10^5$ spores/ml and the culture is divided. The test compound is added to one culture to a final concentration of 20–100 $\mu$g/ml. Solvent only is added to the second culture. The plates are incubated at 25° C. for seven days and optical density measurements at 590 nm are taken daily. The growth curves of the solvent control sample and the test compound sample are compared. A test compound is an antibiotic candidate if the growth of the culture containing the test compound is less than the growth of the control culture.

Example 10

Assays for Testing Inhibitors or Candidates for Inhibition of 3-Isopropylmalate Dehydratase Activity The enzymatic activity of 3-Isopropylmalate dehydratase is determined in the presence and absence of candidate compounds in a suitable reaction mixture, such as described by Satyanarayana et al. ((1968B) J Bacteriol 96: 2018–24 (PMID: 5724970)) and/or Kohlhaw ((1988) Methods Enzymol 166: 423–9 (PMID: 3071717)). Candidate compounds are identified when a decrease in products or a lack of decrease in substrates is detected with the reaction proceeding in either direction.

Additionally, the enzymatic activity of a polypeptide comprising 10–50 amino acids from the *M. grisea* 3-Isopropylmalate dehydratase is determined in the presence and absence of candidate compounds in a suitable reaction mixture, such as described by Satyanarayana et al. ((1968B) J Bacteriol 96: 2018–24 (PMID: 5724970)) and/or Kohlhaw ((1988) Methods Enzymol 166: 423–9 (PMID: 3071717)). A polypeptide comprising 10–50 amino acids is generated by subcloning a portion of the IPMD1 gene into a protein expression vector that adds a His-Tag when expressed (see Example 8). Oligonucleotide primers are designed to amplify a portion of the IPMD1 gene using polymerase chain reaction amplification method. The DNA fragment encoding a polypeptide of 10–50 amino acids is cloned into an expression vector, expressed and purified as described in Example 8 above.

Test compounds identified as inhibitors of IPMD1 activity are further tested for antibiotic activity. *Magnaporthe grisea* fungal cells are grown under standard fungal growth conditions that are well known and described in the art. *M. grisea* is grown as described for spore production on oatmeal agar media (Talbot et al. (1993) Plant Cell 5: 1575–1590 (PMID: 8312740)). Spores are harvested into minimal media (Talbot et al. (1993) Plant Cell 5: 1575–1590 (PMID: 8312740)) to a concentration of $2\times10^5$ spores/ml and the culture is divided. The test compound is added to one culture to a final concentration of 20–100 $\mu$g/ml. Solvent only is added to the second culture. The plates are incubated at 25° C. for seven days and optical density measurements at 590 nm are taken daily. The growth curves of the solvent control sample and the test compound sample are compared. A test compound is an antibiotic candidate if the growth of the culture containing the test compound is less than the growth of the control culture.

Example 11

Assays for Testing Compounds for Alteration of 3-Isopropylmalate Dehydratase Gene Expression

*Magnaporthe grisea* fungal cells are grown under standard fungal growth conditions that are well known and described in the art. Wild-type *M. grisea* spores are harvested from cultures grown on complete agar or oatmeal agar media after growth for 10–13 days in the light at 25° C. using a moistened cotton swab. The concentration of spores is determined using a hemacytometer and spore suspensions are prepared in a minimal growth medium to a concentration of $2\times10^5$ spores per ml. 25 ml cultures are prepared to which test compounds will be added at various concentrations. A culture with no test compound present is included as a control. The cultures are incubated at 25° C. for 3 days after which test compound or solvent only control is added. The cultures are incubated an additional 18 hours. Fungal mycelia is harvested by filtration through Miracloth (CalBiochem®, La Jolla, Calif.), washed with water and frozen in liquid nitrogen. Total RNA is extracted with TRIZOL® Reagent using the methods provided by the manufacturer (Life Technologies, Rockville, Md.). Expression is analyzed by Northern analysis of the RNA samples as described (Sambrook et al. (1989) *Molecular Cloning, a Laboratory Manual*, Cold Spring Harbor Laboratory Press) using a radiolabeled fragment of the IPMD1 gene as a probe. Test compounds resulting in a reduced level of IPMD1 mRNA relative to the untreated control sample are identified as candidate antibiotic compounds.

Example 12

In Vivo Cell Based Assay Screening Protocol with a Fungal Strain Containing a Mutant Form of 3-Isopropylmalate Dehydratase with No Activity

*Magnaporthe grisea* fungal cells containing a mutant form of the IPMD1 gene which abolishes enzyme activity, such as a gene containing a transposon insertion (see Examples 4 and 5), are grown under standard fungal growth conditions that are well known and described in the art. *Magnaporthe grisea* spores are harvested from cultures grown on complete agar medium containing 4 mM L-leucine (Sigma-Aldrich Co.) after growth for 10–13 days in the light at 25° C. using a moistened cotton swab. The concentration of spores is determined using a hemacytometer and spore suspensions are prepared in a minimal growth medium containing 100 $\mu$M L-leucine to a concentration of $2\times10^5$ spores per ml. Approximately $4\times10^4$ spores are added to each well of 96-well plates to which a test compound is added (at varying concentrations). The total volume in each well is 200 $\mu$l. Wells with no test compound present (growth control), and wells without cells are included as controls (negative control). The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 13

In Vivo Cell Based Assay Screening Protocol with a Fungal Strain Containing a Mutant Form of 3-Isopropylmalate Dehydratase with Reduced Activity

*Magnaporthe grisea* fungal cells containing a mutant form of the IPMD1 gene, such as a promoter truncation that reduces expression, are grown under standard fungal growth conditions that are well known and described in the art. A promoter truncation is made by deleting a portion of the promoter upstream of the transcription start site using standard molecular biology techniques that are well known and described in the art (Sambrook et al. (1989) *Molecular Cloning, a Laboratory Manual*, Cold Spring Harbor Laboratory Press). *Magnaporthe grisea* spores are harvested from cultures grown on complete agar medium containing 4 mM L-leucine (Sigma-Aldrich Co.) after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores are added to each well of 96-well plates to which a test compound is added (at varying concentrations). The total volume in each well is 200 $\mu$l. Wells with no test compound present (growth control), and wells without cells are included as controls (negative control). The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild-type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 14

In Vivo Cell Based Assay Screening Protocol with a Fungal Strain Containing a Mutant Form of a L-leucine Biosynthetic Gene with No Activity

*Magnaporthe grisea* fungal cells containing a mutant form of a gene in the L-leucine biosynthetic pathway (e.g. a 3-Isopropylmala dehydrogenase (E. C. 1.1.1.85)) are grown under standard fungal growth conditions that are well known and described in the art. *Magnaporthe grisea* spores are harvested from cultures grown on complete agar medium containing 4 mM L-leucine (Sigma-Aldrich Co.) after growth for 10–13 days in the light at 25° C. using a moistened cotton swab. The concentration of spores is determined using a hemacytometer and spore suspensions are prepared in a minimal growth medium containing 100 $\mu$M L-leucine to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 $\mu$l. Wells with no test compound present, and wells without cells are included as controls. The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)×100. The percent of growth inhibition as a result of a test compound on a fungal strain and that on the wild type cells are compared. Compounds that show differential growth inhibition between the mutant and the wild-type are identified as potential antifungal compounds. Similar protocals may be found in Kirsch and DiDomenico ((1994) Biotechnology 26: 177–221 (PMID: 7749303)).

Example 15

In Vivo Cell Based Assay Screening Protocol with a Fungal Strain Containing a Mutant Form of a L-leucine Biosynthetic Gene with Reduced Activity

*Magnaporthe grisea* fungal cells containing a mutant form of a gene in the L-leucine biosynthetic pathway (e.g. a 3-Isopropylmala dehydrogenase (E.C. 1.1.1.85)), such as a promoter truncation that reduces expression, are grown under standard fungal growth conditions that are well known and described in the art. A promoter truncation is made by deleting a portion of the promoter upstream of the transcription start site using standard molecular biology techniques that are well known and described in the art (Sambrook et al. (1989) *Molecular Cloning, a Laboratory Manual*, Cold Spring Harbor Laboratory Press). *Magnaporthe grisea* fungal cells containing a mutant form of are grown under standard fungal growth conditions that are well known and described in the art. *Magnaporthe grisea* spores are harvested from cultures grown on complete agar medium containing 4 mM L-leucine (Sigma-Aldrich Co.) after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 $\mu$l. Wells with no test compound present, and wells without cells are included as controls. The plates are incubated at 25° C. for seven days and optical density measurements at 590 nm are taken daily. Wild type cells are screened under the same conditions. The effect of each compound on the mutant and wild-type fungal strains is measured against the growth control and the percent of inhibition is calculated as the $OD_{590}$ (fungal strain plus test compound)/$OD_{590}$ (growth control)x100. The percent of growth inhibition as a result of a test compound on a fungal strain and that on the wild type cells are compared. Compounds that show differential growth inhibition between the mutant and the wild type are identified as potential antifungal compounds. Similar protocols may be found in Kirsch and DiDomenico ((1994) Biotechnology 26: 177–221 (PMID: 7749303)).

Example 16

In Vivo Cell Based Assay Screening Protocol with a Fungal Strain Containing a Fungal IPMD1 and a Second Fungal Strain Containing a Heterologous IPMD1 Gene Wild-type *Magnaporthe grisea* fungal cells and *M. grisea* fungal cells lacking a functional IPMD1 gene and containing a 3-isopropylmalate dehydratase large subunit gene from *Xylella fastidiosa* (Genbank accession number H82564, 63% sequence identity) are grown under standard fungal growth conditions that are well known and described in the art. A *M. grisea* strain carrying a heterologous IPMD1 gene is made as follows:

A *M. grisea* strain is made with a nonfunctional IPMD1 gene, such as one containing a transposon insertion in the native gene (see Examples 4 and 5).

A construct containing a heterologous IPMD1 gene is made by cloning the 3-isopropylmalate dehydratase large subunit gene from *Xylella fastidiosa* into a fungal expression vector containing a trpC promoter and terminator (e.g. pCB1003, Carroll et al. (1994) Fungal Gen News Lett 41: 22) using standard molecular biology techniques that are well known and described in the art (Sambrook et al. (1989) *Molecular Cloning, a Laboratory Manual*, Cold Spring Harbor Laboratory Press).

The said construct is used to transform the *M. grisea* strain lacking a functional IPMD1 gene (see Example 5). Transformants are selected on minimal agar medium lacking L-leucine. Only transformants carrying a functional IPMD1 gene will grow.

Wild-type strains of *Magnaporthe grisea* and strains containing a heterologous form of IPMD1 are grown under standard fungal growth conditions that are well known and described in the art. *Magnaporthe grisea* spores are harvested from cultures grown on complete agar medium after growth for 10–13 days in the light at 25° C. using a moistened cotton swab. The concentration of spores is determined using a hemacytometer and spore suspensions are prepared in a minimal growth medium to a concentration of $2\times10^5$ spores per ml. Approximately $4\times10^4$ spores or cells are harvested and added to each well of 96-well plates to which growth media is added in addition to an amount of test compound (at varying concentrations). The total volume in each well is 200 μl. Wells with no test compound present, and wells without cells are included as controls. The plates are incubated at 25° C. for seven days and optical density measurements at 590 nm are taken daily. The effect of each compound on the wild-type and heterologous fungal strains is measured against the growth control and the percent of inhibition is calculated as the $OD_{590}$ (fungal strain plus test compound)/$OD_{590}$ (growth control)x100. The percent of growth inhibition as a result of a test compound on the wild-type and heterologous fungal strains are compared. Compounds that show differential growth inhibition between the wild-type and heterologous strains are identified as potential antifungal compounds with specificity to the native or heterologous IPMD1 gene products. Similar protocols may be found in Kirsch and DiDomenico ((1994) Biotechnology 26: 177–221 (PMID: 7749303)).

Example 17

Pathway Specific In Vivo Assay Screening Protocol

*Magnaporthe grisea* fungal cells are grown under standard fungal growth conditions that are well known and described in the art. Wild-type *M. grisea* spores are harvested from cultures grown on oatmeal agar media after growth for 10–13 days in the light at 25° C. using a moistened cotton swab. The concentration of spores is determined using a hemocytometer and spore suspensions are prepared in a minimal growth medium and a minimal growth medium containing 4 mM L-leucine (Sigma-Aldrich Co.) to a concentration of $2\times10^5$ spores per ml. The minimal growth media contains carbon, nitrogen, phosphate, and sulfate sources, and magnesium, calcium, and trace elements (for example, see inoculating fluid in Example 7). Spore suspensions are added to each well of a 96-well microtiter plate (approximately $4\times10^4$ spores/well). For each well containing a spore suspension in minimal media, an additional well is present containing a spore suspension in minimal medium containing 4 mM L-leucine. Test compounds are added to wells containing spores in minimal media and minimal media containing L-leucine. The total volume in each well is 200 μl. Bot containing media wells with no test compound are provided as controls. The plates are incubated at 25° C. for seven days and optical density measurements at 590 nm are taken daily. A compound is identified as a candidate for an antibiotic acting against the L-leucine biosynthetic pathway when the observed growth in the well containing minimal media is less than the observed growth in the well containing L-leucine as a result of the addition of the test compound. Similar protocols may be found in Kirsch and DiDomenico ((1994) Biotechnology 26: 177–221 (PMID: 7749303)).

While the foregoing describes certain embodiments of the invention, it will be understood by those skilled in the art that variations and modifications may be made and still fall within the scope of the invention. The foregoing examples are intended to exemplify various specific embodiments of the invention and do not limit its scope in any manner.

What is claimed is:

1. A method for identifying a test compound as a candidate for an antibiotic, comprising:

a) contacting 2-Isopropylmalate and $H_2O$ with a *Magnaporthe grisea* 3-Isopropylmalate dehydratase;

b) contacting 2-Isopropylmalate and $H_2O$ with the *Magnaporthe grisea* 3-Isopropylmalate dehydratase and a test compound; and c) determining the change in concentration for at least one of the following: 2-Isopropylmalate, $H_2O$, and/or 3-Isopropylmalate, wherein a change in concentration for any of the above substances between steps (a) and (b) indicates that said test compound is a candidate for an antibiotic.

2. The method of claim 1, wherein said 3-Isopropylmalate dehydratase is SEQ ID NO:3.

3. A method for identifying a test compound as a candidate for an antibiotic, comprising:

a) contacting 3-Isopropylmalate with a *Magnaporthe grisea* 3-Isopropylmalate dehydratase;

b) contacting 3-Isopropylmalate with the *Magnaporthe grisea* 3-Isopropylmalate dehydratase and a test compound; and c) determining the change in concentration for at least one of the following: 2-Isopropylmalate, $H_2O$, and/or 3-Isopropylmalate, wherein a change in concentration for any of the above substances between steps (a) and (b) indicates that said test compound is a candidate for an antibiotic.

4. The method of claim 3, wherein said 3-Isopropylmalate dehydratase is SEQ ID NO: 3.

* * * * *

SEQUENCE LISTING

```
<160> NUMBER OF SEQ ID NOS: 3

<210> SEQ ID NO 1
<211> LENGTH: 2337
<212> TYPE: DNA
```

-continued

<213> ORGANISM: Magnaporthe grisea

<400> SEQUENCE: 1

```
atgcctggag cagaaagcac tccgcagacc ttgtacgaca aggttctgca agcacacgtg     60
gtcgatgaga agctcgacgg cacagtcctc ttgtacatcg accgccacct tgtacatgag    120
gtcacatcac ctcaagcatt cgagggcctc aggaatgcag gccgtaaagt gcggagaccc    180
gactgcacct tggccaccac agaccataac gtccccacga cttcacggaa agctctcaag    240
gacattgcca gcttcatcaa agaggacgac tcaaggaccc aatgtgtgac tctggaggaa    300
aatgtcaagg agtttggcgt cacatatttt ggcctcagcg acaagcgcca gggtattgtg    360
cacgtcattg gccctgagca aggcttcacg ctccccggaa caacggttgt gtgtggagac    420
agtcacacgt ctacccatgg cgcctttgga gcccttgcct ttggtatcgg taccagcgag    480
gttgagcacg tgctggccac tcagtgcttg atcaccaaga ggagcaagaa catgaggata    540
caagtcgacg gcgagctggc tcctggtgtc agctccaagg atgtcgtgct tcatgcaatc    600
ggtatcattg gtaccgctgg aggcaccggg gctgtcatcg agttctgtgg ttccgtcatc    660
cgcagcctca gcatggaggc ccgcatgtca atctgcaaca tgtccatcga gggaggtgcc    720
agggctggca tggtagcccc tgacgagatc accttcgaat acctcaaggg ccgcccgctc    780
gctccgaagt acgactcgcc cgagtggcac aaggctaccc aatactggaa gaaccttcag    840
tccgacccag gtgccaaata cgatattgat gtctttattg acgccaaaga cattgtacca    900
accttgacat ggggcacaag tcccgaggat gttgttccga tcaccggcgt tgttcctgat    960
cctgagacgt ttgctaccga agcgaagaag gcggacgggc gacgcatgct gcagtacatg   1020
ggactgaagg cgggtactcc catggaggac attccggtcg acaaagtctt catcggctcc   1080
tgcaccaatt ccaggattga ggatctccgt gctgctgccg cggtcgtaaa gggccggaaa   1140
aaagcaccca atgttaagag cgccatggtg gtgccgggat cgggcttggt caagactcaa   1200
gctgaggagg aaggcctgga caagattttt gaggaggccg gctttgaatg gcgcgaggct   1260
ggctgcagta tgtgccttgg catgaaccca gatattctcg ctccccagga gcgttgtgcc   1320
agtaccagca accgcaactt cgagggtcgc cagggtgcag gcggccgcac tcatctcatg   1380
tccccagtca tggctgctgc tgctggtatc gtcggtaagc ttgcagatgt gagaaagttg   1440
accgattaca aggccagccc tcacattgca gcttaccaga aatcgacagt gacaaagccc   1500
catgtggatg agcggatcaa ccaagatgcg catgagaaag atatcattgc tgatattcct   1560
gaggacaaca acggccctca caccaacacc tctgccagtg ttggcacttc agcagggctt   1620
cccaagttca ccattctcaa gggtatagcg gctccgctgg agaaggctaa tgttgacacc   1680
gacgccatca ttcccaaaca atttctcaag acaatcaaga ggacaggcct tggaaatgct   1740
ctgttctatg agatgaggtt caatgaggac ggcactgaga agagcgactt tgttctcaac   1800
aaggagccgt accggaaagc cagtattctg gtttgcacgg gtgccaactt tggatgtggg   1860
agctctcgtg agcatgcgcc atgggctctc aacgattttg gcatcaggag cgtcattgcc   1920
ccgtcgttcg cagatatatt cttcaacaac tccttcaaga acggcatgct gccgatccct   1980
atcaaggacc aggctcagat cgaggccatc gccgccgaag ccagggcggg caaggaaatc   2040
gaagttgacc tcccaaacca gctgatcaag aacgcaaccg gcgagacgat ctgcactttc   2100
gaggtggagg agtttaggaa gcactgcttg gtcaatggtc tcgatgatat cggcttgacc   2160
atgcagatgg aagacaagat cgccgagttc gaggccaaga tgaccaggga gactccctgg   2220
ctcgacggaa ctggctacct caagcgaaag ggtcaaggtg gtaagctcgc agccaaggct   2280
```

-continued gtgcccgtgc ctaccaccaa caggggcgag gagaagaagg agccgcttga gtggtga 2337

<210> SEQ ID NO 2
<211> LENGTH: 3235
<212> TYPE: DNA
<213> ORGANISM: Magnaporthe grisea

<400> SEQUENCE: 2
agttaaagga aacccgcgtc gaggtctact agaatccggc actccgatat cgccattgaa 60
tctgcgacga cagcaagttc aaaaaagaac attcaagaca aaaaagagct accgtctttc 120
taactttccc ctcctaacct atcttcgccc gttcgtctga attcaatcat tttttattgt 180
tgattgcttt gtgtgatcct gccactttcc tacacgaaca aaacccggcg accatattga 240
cctaccggct tcttctccaa ctacatctgt cttgacccta ttttgtttgc gtggtgtcaa 300
tcattcgtga taccgacttt cagtcctttc cagattccaa aaaaaatgcc tggagcagaa 360
agcactccgc agaccttgta cgacaaggtt ctgcaagcac acgtggtcga tgagaagctc 420
gacggcacag tcctcttgta catcggttcg tagcctgacc atcggggcta ggccccagct 480
tggagtggca ccaagcagca gcttttgtca actgaccagg tctctttgct tttgtagacc 540
gccaccttgt acatgaggtc acatcacctg taagaaaccc agcccacgga ccacaagcaa 600
gccgcgaaac caagccacta tattaacgca acgaaacggg cgctaacatg tttgaatgac 660
tactagcaag cattcgaggg cctcaggaat gcaggccgta aagtgcggag acccgactgc 720
accttggcca ccacagacca tgtaagtgaa gaagacctgt ataaaatctc cactccgata 780
tcggctgcaa aagctaaccc ttctttttgt catcgcccat gctagaacgt ccccacgact 840
tcacggaaag ctctcaagga cattgccagc ttcatcaaag aggacgactc aaggacccaa 900
tgtgtgactc tggaggaaaa tgtcaaggag tttggcgtca catattttgg cctcagcgac 960
aagcgccagg gtattgtgca cgtcattggc cctgagcaag gcttcacgct ccccggaaca 1020
acggttgtgt gtggagacag tcacacgtct acccatggcg cctttggagc ccttgccttt 1080
ggtatcggta ccagcgaggt tgagcacgtg ctggccactc agtgcttgat caccaagagg 1140
agcaagaaca tgaggataca agtcgacggc gagctggctc ctggtgtcag ctccaaggat 1200
gtcgtgcttc atgcaatcgg tatcattggt accgctggag gcaccggggc tgtcatcgag 1260
ttctgtggtt ccgtcatccg cagcctcagc atggaggccc gcatgtcaat ctgcaacatg 1320
tccatcgagg gaggtgccag ggctggcatg gtagcccctg acgagatcac cttcgaatac 1380
ctcaagggcc gcccgctcgc tccgaagtac gactcgcccg agtggcacaa ggctacccaa 1440
tactggaaga accttcagtc cgacccaggt gccaaatacg atattgatgt ctttattgac 1500
gccaaagaca ttgtaccaac cttgacatgg ggcacaagtc ccgaggatgt tgttccgatc 1560
accggcgttg ttcctgatcc tgagacgttt gctaccgaag cgaagaaggc ggacgggcga 1620
cgcatgctgc agtacatggg actgaaggcg ggtactccca tggaggacat tccggtcgac 1680
aaagtcttca tcggctcctg caccaattcc aggattgagg atctccgtgc tgctgccgcg 1740
gtcgtaaagg gccggaaaaa agcacccaat gttaagagcg ccatggtggt gccgggatcg 1800
ggcttggtca agactcaagc tgaggaggaa ggcctggaca agatttttga ggaggccggc 1860
tttgaatggc gcgaggctgg ctgcagtatg tgccttggca tgaacccaga tattctcgct 1920
ccccaggagc gttgtgccag taccagcaac cgcaacttcg agggtcgcca gggtgcaggc 1980
ggccgcactc atctcatgtc cccagtcatg gctgctgctg ctggtatcgt cggtaagctt 2040

-continued

```
gcagatgtga gaaagttgac cgattacaag gccagccctc acattgcagc ttaccagaaa   2100

tcgacagtga caaagcccca tgtggatgag cggatcaacc aagatgcgca tgagaaagat   2160

atcattgctg atattcctga ggacaacaac ggccctcaca ccaacacctc tgccagtgtt   2220

ggcacttcag cagggcttcc caagttcacc attctcaagg gtatagcggc tccgctggag   2280

aaggctaatg ttgacaccga cgccatcatt cccaaacaat ttctcaagac aatcaagagg   2340

acaggccttg gaaatgctct gttctatgag atgaggttca atgaggacgg cactgagaag   2400

agcgactttg ttctcaacaa ggagccgtac cggaaagcca gtattctggt ttgcacgggt   2460

gccaactttg gatgtgggag ctctcgtgag catgcgccat gggctctcaa cgattttggc   2520

atcaggagcg tcattgcccc gtcgttcgca gatatattct tcaacaactc cttcaagaac   2580

ggcatgctgc cgatccctat caaggaccag gctcagatcg aggccatcgc cgccgaagcc   2640

agggcgggca aggaaatcga agttgacctc ccaaaccagc tgatcaagaa cgcaaccggc   2700

gagacgatct gcactttcga ggtggaggag tttaggaagc actgcttggt caatggtctc   2760

gatgatatcg gcttgaccat gcagatggaa gacaagatcg ccgagttcga ggccaagatg   2820

accagggaga ctccctggct cgacggaact ggctacctca agcgaaaggg tcaaggtggt   2880

aagctcgcag ccaaggctgt gcccgtgcct accaccaaca ggggcgagga gaagaaggag   2940

ccgcttgagt ggtgacggct tcctaacgaa gtgttgtcga aaacgaaagg cgttaatcgg   3000

ttcaactggt gaaaactatt attcggttgg gatttatgaa ataaccctgc gaaagggact   3060

ctcgttgagc ttgcgattat tgtactgcga tatcagtgtg ggaaattttc tgcgtcagac   3120

tttactgtaa tgctcttctt cttcaagaaa gatcttagtg ttttgatttt ctacaatgag   3180

acgaccaata cacaaaccgc ctggtcatta aaaaaaaaaa aaaaaactcg agggg        3235


<210> SEQ ID NO 3
<211> LENGTH: 778
<212> TYPE: PRT
<213> ORGANISM: Magnaporthe grisea

<400> SEQUENCE: 3

Met Pro Gly Ala Glu Ser Thr Pro Gln Thr Leu Tyr Asp Lys Val Leu
1               5                   10                  15

Gln Ala His Val Val Asp Glu Lys Leu Asp Gly Thr Val Leu Leu Tyr
            20                  25                  30

Ile Asp Arg His Leu Val His Glu Val Thr Ser Pro Gln Ala Phe Glu
        35                  40                  45

Gly Leu Arg Asn Ala Gly Arg Lys Val Arg Arg Pro Asp Cys Thr Leu
    50                  55                  60

Ala Thr Thr Asp His Asn Val Pro Thr Thr Ser Arg Lys Ala Leu Lys
65                  70                  75                  80

Asp Ile Ala Ser Phe Ile Lys Glu Asp Asp Ser Arg Thr Gln Cys Val
                85                  90                  95

Thr Leu Glu Glu Asn Val Lys Glu Phe Gly Val Thr Tyr Phe Gly Leu
            100                 105                 110

Ser Asp Lys Arg Gln Gly Ile Val His Val Ile Gly Pro Glu Gln Gly
        115                 120                 125

Phe Thr Leu Pro Gly Thr Thr Val Val Cys Gly Asp Ser His Thr Ser
    130                 135                 140

Thr His Gly Ala Phe Gly Ala Leu Ala Phe Gly Ile Gly Thr Ser Glu
145                 150                 155                 160

Val Glu His Val Leu Ala Thr Gln Cys Leu Ile Thr Lys Arg Ser Lys
```

-continued

```
                165                 170                 175

Asn Met Arg Ile Gln Val Asp Gly Glu Leu Ala Pro Gly Val Ser Ser
            180                 185                 190

Lys Asp Val Val Leu His Ala Ile Gly Ile Ile Gly Thr Ala Gly Gly
        195                 200                 205

Thr Gly Ala Val Ile Glu Phe Cys Gly Ser Val Ile Arg Ser Leu Ser
    210                 215                 220

Met Glu Ala Arg Met Ser Ile Cys Asn Met Ser Ile Glu Gly Gly Ala
225                 230                 235                 240

Arg Ala Gly Met Val Ala Pro Asp Glu Ile Thr Phe Glu Tyr Leu Lys
                245                 250                 255

Gly Arg Pro Leu Ala Pro Lys Tyr Asp Ser Pro Glu Trp His Lys Ala
            260                 265                 270

Thr Gln Tyr Trp Lys Asn Leu Gln Ser Asp Pro Gly Ala Lys Tyr Asp
        275                 280                 285

Ile Asp Val Phe Ile Asp Ala Lys Asp Ile Val Pro Thr Leu Thr Trp
    290                 295                 300

Gly Thr Ser Pro Glu Asp Val Val Pro Ile Thr Gly Val Val Pro Asp
305                 310                 315                 320

Pro Glu Thr Phe Ala Thr Glu Ala Lys Lys Ala Asp Gly Arg Arg Met
                325                 330                 335

Leu Gln Tyr Met Gly Leu Lys Ala Gly Thr Pro Met Glu Asp Ile Pro
            340                 345                 350

Val Asp Lys Val Phe Ile Gly Ser Cys Thr Asn Ser Arg Ile Glu Asp
        355                 360                 365

Leu Arg Ala Ala Ala Ala Val Val Lys Gly Arg Lys Lys Ala Pro Asn
    370                 375                 380

Val Lys Ser Ala Met Val Val Pro Gly Ser Gly Leu Val Lys Thr Gln
385                 390                 395                 400

Ala Glu Glu Glu Gly Leu Asp Lys Ile Phe Glu Glu Ala Gly Phe Glu
                405                 410                 415

Trp Arg Glu Ala Gly Cys Ser Met Cys Leu Gly Met Asn Pro Asp Ile
            420                 425                 430

Leu Ala Pro Gln Glu Arg Cys Ala Ser Thr Ser Asn Arg Asn Phe Glu
        435                 440                 445

Gly Arg Gln Gly Ala Gly Gly Arg Thr His Leu Met Ser Pro Val Met
    450                 455                 460

Ala Ala Ala Ala Gly Ile Val Gly Lys Leu Ala Asp Val Arg Lys Leu
465                 470                 475                 480

Thr Asp Tyr Lys Ala Ser Pro His Ile Ala Ala Tyr Gln Lys Ser Thr
                485                 490                 495

Val Thr Lys Pro His Val Asp Glu Arg Ile Asn Gln Asp Ala His Glu
            500                 505                 510

Lys Asp Ile Ile Ala Asp Ile Pro Glu Asp Asn Asn Gly Pro His Thr
        515                 520                 525

Asn Thr Ser Ala Ser Val Gly Thr Ser Ala Gly Leu Pro Lys Phe Thr
    530                 535                 540

Ile Leu Lys Gly Ile Ala Ala Pro Leu Glu Lys Ala Asn Val Asp Thr
545                 550                 555                 560

Asp Ala Ile Ile Pro Lys Gln Phe Leu Lys Thr Ile Lys Arg Thr Gly
                565                 570                 575

Leu Gly Asn Ala Leu Phe Tyr Glu Met Arg Phe Asn Glu Asp Gly Thr
            580                 585                 590
```

-continued

```
Glu Lys Ser Asp Phe Val Leu Asn Lys Glu Pro Tyr Arg Lys Ala Ser
        595                 600                 605

Ile Leu Val Cys Thr Gly Ala Asn Phe Gly Cys Gly Ser Ser Arg Glu
    610                 615                 620

His Ala Pro Trp Ala Leu Asn Asp Phe Gly Ile Arg Ser Val Ile Ala
625                 630                 635                 640

Pro Ser Phe Ala Asp Ile Phe Phe Asn Asn Ser Phe Lys Asn Gly Met
                645                 650                 655

Leu Pro Ile Pro Ile Lys Asp Gln Ala Gln Ile Glu Ala Ile Ala Ala
            660                 665                 670

Glu Ala Arg Ala Gly Lys Glu Ile Glu Val Asp Leu Pro Asn Gln Leu
        675                 680                 685

Ile Lys Asn Ala Thr Gly Glu Thr Ile Cys Thr Phe Glu Val Glu Glu
    690                 695                 700

Phe Arg Lys His Cys Leu Val Asn Gly Leu Asp Asp Ile Gly Leu Thr
705                 710                 715                 720

Met Gln Met Glu Asp Lys Ile Ala Glu Phe Glu Ala Lys Met Thr Arg
                725                 730                 735

Glu Thr Pro Trp Leu Asp Gly Thr Gly Tyr Leu Lys Arg Lys Gly Gln
            740                 745                 750

Gly Gly Lys Leu Ala Ala Lys Ala Val Pro Val Pro Thr Thr Asn Arg
        755                 760                 765

Gly Glu Glu Lys Lys Glu Pro Leu Glu Trp
    770                 775
```